United States Patent [19]

Kanno et al.

[11] Patent Number: 6,159,901
[45] Date of Patent: Dec. 12, 2000

[54] 6-PHENOXY PICOLINIC ACID ALKYLIDENE HYDRAZIDE DERIVATIVE, PROCESS FOR PRODUCING THE SAME AND HERBICIDE USING THE SAME

[75] Inventors: Hisashi Kanno; Kazuo Yoshida; Tsutomu Sato, all of Iwaki; Koki Sato, Fukushima; Yoichi Kanda, Iwaki, all of Japan

[73] Assignee: Kureha Kagaku Kogyo Kabushiki Kaisha, Tokyo, Japan

[21] Appl. No.: 09/446,588

[22] PCT Filed: Jun. 25, 1998

[86] PCT No.: PCT/JP98/02842

§ 371 Date: Feb. 23, 2000

§ 102(e) Date: Feb. 23, 2000

[87] PCT Pub. No.: WO99/00370

PCT Pub. Date: Jan. 7, 1999

[30] Foreign Application Priority Data

Jun. 27, 1997 [JP] Japan ................................ 9-187353

[51] Int. Cl.$^7$ .......................... A01N 43/00; A01N 43/46; A01N 43/72; A01N 43/84; A01N 43/40
[52] U.S. Cl. .......................... 504/209; 504/218; 504/221; 504/223; 504/244; 504/251; 504/254; 504/256; 504/257; 546/298; 546/296
[58] Field of Search ...................... 546/325, 298, 546/296; 504/209, 218, 221, 223, 244, 251, 254, 255, 256, 257

[56] References Cited

U.S. PATENT DOCUMENTS 5,384,305  1/1995  Foster et al. .

FOREIGN PATENT DOCUMENTS

| 4-290805 | 10/1992 | Japan . |
| 2277930 | 11/1994 | United Kingdom . |
| WO 96/06096 A1 | 2/1996 | WIPO . |
| WO 97/24330 A1 | 7/1997 | WIPO . |

*Primary Examiner*—Thurman K. Page
*Assistant Examiner*—Binta Robinson
*Attorney, Agent, or Firm*—Nixon & Vanderhye

[57] ABSTRACT

A 6-phenoxy picolinic acid alkylidene hydrazide derivative, a process for producing the derivative and a herbicide containing the derivative as an effective ingredient. Such a compound is a novel compound and is useful as an effective ingredient of herbicides.

3 Claims, No Drawings

6-PHENOXY PICOLINIC ACID ALKYLIDENE HYDRAZIDE DERIVATIVE, PROCESS FOR PRODUCING THE SAME AND HERBICIDE USING THE SAME

This application is a 371 of PCT/JP98/02842 filed Jun. 25, 1998.

TECHNICAL FIELD

The present invention relates to a 6-phenoxy picolinic acid alkylidene hydrazide derivative, a process for producing the derivative and a herbicide containing the derivative as an effective ingredient.

BACKGROUND ART

The 6-phenoxy picolinic acid alkylidene hydrazide derivative according to the present invention is a novel compound which has never been described in any literature.

Hitherto, it has been highly demanded to provide a herbicide capable of lessening the amount existing or remaining in environment after use and exhibiting an excellent herbicidal effect even when used in a small amount; a herbicide capable of exhibiting an excellent herbicidal effect with a high selectivity between crops and weeds irrespective of change of environmental conditions; and a herbicide which is free from phytotoxicity or chemical injury even upon the succeeding crop of double cropping.

DISCLOSURE OF THE INVENTION

The present invention have been made in order to meet the above-described demands. It is an object of the present invention to provide a novel compound which can exhibit an excellent selective herbicidal effect even when used in a small amount and is free from phytotoxicity or chemical injury even upon the succeeding crop of double cropping, a process for producing such a compound, and a novel herbicide containing the compound as an effective ingredient.

As a result of the present inventors' earnest studies for developing a novel industrially useful pyridine derivative, it has been found that 6-phenoxy picolinic acid alkylidene hydrazide derivative as a novel compound which has never been described in any patent documents or literatures, can exhibit an excellent herbicidal effect. The present invention has been attained on the basis of this finding.

That is, in a first aspect of the present invention, there is provided a 6-phenoxy picolinic acid alkylidene hydrazide derivative represented by the general formula (I):

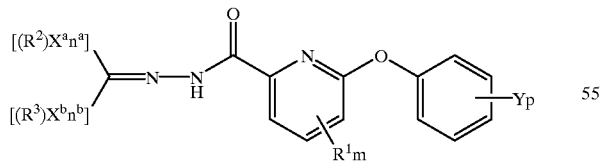

(I)

wherein $R^1$ is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group, a $C_1$ to $C_4$ dialkylamino group or a ($C_1$ to $C_4$ alkyl) ($C_7$ to $C_8$ aralkyl)amino group;

m is an integer of 0 to 3;

$R^2$ and $R^3$ are independently a hydrogen atom or a group which may be substituted with $X^a$ or $X^b$, said group being a $C_1$ to $C_{10}$ alkyl group, a $C_2$ to $C_6$ alkenyl group, a $C_2$ to $C_6$ alkynyl group, a $C_3$ to $C_6$ cycloalkyl group, a phenyl group or an arylalkyl group (whose alkyl moiety has 1 to 3 carbon atoms) [wherein the chain hydrocarbon moiety of each of $R^2$ and $R^3$ is constituted by a longest carbon chain as a main chain, a $C_1$ to $C_4$ alkyl group bonded as a side chain to said main chain is excluded from $R^2$ and $R^3$, and said $C_1$ to $C_4$ alkyl group as a side chain is regarded as substituent of each of $R^2$ and $R^3$];

$X^a$ and $X^b$ are a halogen atom, a $C_1$ to $C_4$ alkoxy group, a $C_1$ to $C_4$ alkylthio group, a $C_1$ to $C_4$ alkyl group (which is not bonded to terminal positions of $R^2$ and $R^3$ when $R^2$ and $R^3$ are a $C_1$ to $C_{10}$ alkyl group), a $C_3$ to $C_6$ cycloalkyl group or a cyano group;

$n^a$ and $n^b$ are 0 or an integer selected from numbers of hydrogen atoms of $R^2$ and $R^3$, respectively, which can be substituted with $X^a$ and $X^b$, respectively;

when both of $R^2$ and $R^3$ are alkyl chains, said $R^2$ and $R^3$ may be directly bonded with each other to form a ring, or said $R^2$ and $R^3$ may be bonded to each other through an oxygen atom, a sulfur atom or a nitrogen atom (the nitrogen atom may be alkylated with a $C_1$ to $C_4$ alkyl group) to form a ring;

Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom; and p is an integer of 0 to 5, and when m, $n^a$, $n^b$ and p are not less than 2, $R^1$s, $X^a$s, $X^b$s and Ys may be the same or different, respectively.

In a second aspect of the present invention, there is provided a process for producing a 6-phenoxy picolinic acid alkylidene hydrazide derivative represented by the general formula (I), comprising:

subjecting a 6-phenoxy picolinic acid hydrazide derivative represented by the general formula (II) and aldehydes or ketones represented by the general formula (III) to dehydrocondensation.

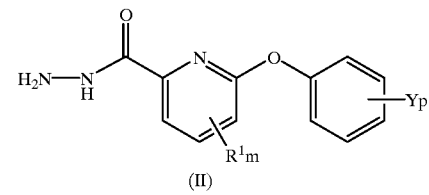

(II)

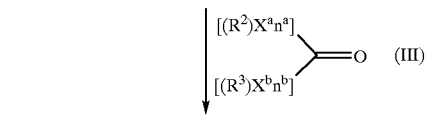

(III)

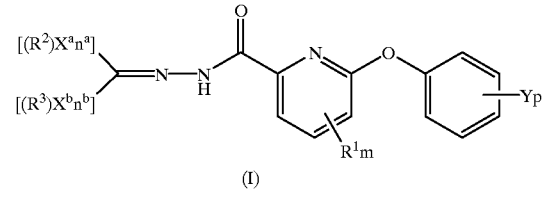

(I)

wherein $R^1$ is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group, a $C_1$ to $C_4$ dialkylamino group or a ($C_1$ to $C_4$ alkyl) ($C_7$ to $C_8$ aralkyl)amino group;

m is an integer of 0 to 3;

$R^2$ and $R^3$ are independently a hydrogen atom or a group which may be substituted with $X^a$ or $X^b$, said group being a $C_1$ to $C_{10}$ alkyl group, a $C_2$ to $C_6$ alkenyl group, a $C_2$ to $C_6$ alkynyl group, a $C_3$ to $C_6$ cycloalkyl group, a phenyl group or an arylalkyl group (whose alkyl moiety has 1 to 3 carbon atoms) [wherein the chain hydrocarbon moiety of each of $R^2$ and $R^3$ is constituted by a longest carbon chain as a main chain, a $C_1$ to $C_4$ alkyl group bonded as a side chain to said main chain is excluded from $R^2$ and $R^3$, and said $C_1$ to $C_4$ alkyl group as a side chain is regarded as substituent of each of $R^2$ and $R^3$];

$X^a$ and $X^b$ are a halogen atom, a $C_1$ to $C_4$ alkoxy group, a $C_1$ to $C_4$ alkylthio group, a $C_1$ to $C_4$ alkyl group (which is not bonded to terminal positions of $R^2$ and $R^3$ when $R^2$ and $R^3$ are a $C_1$ to $C_{10}$ alkyl group), a $C_3$ to $C_6$ cycloalkyl group or a cyano group;

$n^a$ and $n^b$ are 0 or an integer selected from numbers of hydrogen atoms of $R^2$ and $R^3$, respectively, which can be substituted with $X^a$ and $X^b$, respectively;

when both of $R^2$ and $R^3$ are alkyl chains, said $R^2$ and $R^3$ may be directly bonded with each other to form a ring, or said $R^2$ and $R^3$ may be bonded to each other through an oxygen atom, a sulfur atom or a nitrogen atom (the nitrogen atom may be alkylated with a $C_1$ to $C_4$ alkyl group) to form a ring;

Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom; and p is an integer of 0 to 5, and when m, $n^a$, $n^b$ and p are not less than 2, $R^1$s, $X^a$s, $X^b$s and Ys may be the same or different, respectively.

In a third aspect of the present invention, there is provided a herbicide containing a 6-phenoxy picolinic acid alkylidene hydrazide derivative represented by the general formula (I), as an effective ingredient.

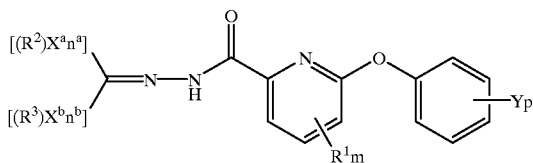

(I)

wherein $R^1$ is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group, a $C_1$ to $C_4$ dialkylamino group or a ($C_1$ to $C_4$ alkyl) ($C_7$ to $C_8$ aralkyl)amino group;

m is an integer of 0 to 3;

$R^2$ and $R^3$ are independently a hydrogen atom or a group which may be substituted with $X^a$ or $X^b$, said group being a $C_1$ to $C_{10}$ alkyl group, a $C_2$ to $C_6$ alkenyl group, a $C_2$ to $C_6$ alkynyl group, a $C_3$ to $C_6$ cycloalkyl group, a phenyl group or an arylalkyl group (whose alkyl moiety has 1 to 3 carbon atoms) [wherein the chain hydrocarbon moiety of each of $R^2$ and $R^3$ is constituted by a longest carbon chain as a main chain, a $C_1$ to $C_4$ alkyl group bonded as a side chain to said main chain is excluded from $R^2$ and $R^3$, and said $C_1$ to $C_4$ alkyl group as a side chain is regarded as substituent of each of $R^2$ and $R^3$];

$X^a$ and $X^b$ are a halogen atom, a $C_1$ to $C_4$ alkoxy group, a $C_1$ to $C_4$ alkylthio group, a $C_1$ to $C_4$ alkyl group (which is not bonded to terminal positions of $R^2$ and $R^3$ when $R^2$ and $R^3$ are a $C_1$ to $C_{10}$ alkyl group), a $C_3$ to $C_6$ cycloalkyl group or a cyano group;

$n^a$ and $n^b$ are 0 or an integer selected from numbers of hydrogen atoms of $R^2$ and $R^3$, respectively, which can be substituted with $X^a$ and $X^b$, respectively;

when both of $R^2$ and $R^3$ are alkyl chains, said $R^2$ and $R^3$ may be directly bonded with each other to form a ring, or said $R^2$ and $R^3$ may be bonded to each other through an oxygen atom, a sulfur atom or a nitrogen atom (the nitrogen atom may be alkylated with a $C_1$ to $C_4$ alkyl group) to form a ring;

Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom; and p is an integer of 0 to 5, and when m, $n^a$, $n^b$ and p are not less than 2, $R^1$s, $X^a$s, $X^b$S and Ys may be the same or different, respectively.

The present invention will be described in detail below.

First, the 6-phenoxy picolinic acid alkylidene hydrazide derivative represented by the above general formula (I) (hereinafter referred to merely as "compound (I)") is explained.

Definitions and specific examples of the respective symbols ($R^1$, $R^2$, $R^3$, $X^a$, $X^b$ and Y) of the compound (I) according to the present specification, are as follows.

With respect to $R^1$, as the halogen atom, there may be exemplified a chlorine atom, a bromine atom, a fluorine atom or the like; as the $C_1$ to $C_4$ alkyl group, there may be exemplified methyl, ethyl or the like; as the $C_1$ to $C_4$ haloalkyl group, there may be exemplified trifluoromethyl or the like; as the $C_1$ to $C_4$ alkoxy group, there may be exemplified methoxy, ethoxy, (1-methyl)ethoxy (same as isopropoxy group) or the like; as the $C_1$ to $C_4$ haloalkoxy group, there may be exemplified trifluoromethoxy, 2,2,2-trifluoroethyloxy or the like; as the $C_1$ to $C_4$ alkylthio group, there may be exemplified methylthio, ethylthio or the like; as the $C_1$ to $C_4$ alkylamino group, there may be exemplified methylamino, ethylamino or the like; as the di($C_1$ to $C_4$ alkyl)amino group, there may be exemplified dimethylamino, ethylmethylamino or the like; and as the ($C_1$ to $C_4$ alkyl) ($C_7$ to $C_8$ aralkyl)amino group, there may be exemplified methyl(phenylmethyl)amino, ethyl (phenylmethyl)amino or the like.

Among the above-defined examples, the preferred substituents as $R^1$ may include chlorine atom, methyl, methoxy, ethoxy, methylthio, ethylthio, methylamino, ethylamino, dimethylamino and methylethylamino.

The symbol m is an integer of usually 0 to 3, preferably 0 to 1, and when m is 1, it is preferred that $R^1$ is bonded to the 4-position of the pyridine ring.

Next, $R^2$ is explained below.

The chain hydrocarbon moiety of $R^2$ is constituted by a longest carbon chain as a main chain. The $C_1$ to $C_4$ alkyl group bonded as a side chain to the main chain, if any, is excluded from $R^2$, and is regarded as the substituent $X^a$.

Namely, with respect to the $C_1$ to $C_{10}$ alkyl group, the longest carbon chain thereof is regarded as $R^2$, and other groups bonded thereto are regarded as substituents. Accordingly, in the case of isopropyl group, the ethyl group is regarded as $R^2$, and the methyl group bonded to the 1-position of the ethyl group is regarded as a substituent. Similarly, in the case of t-butyl group, the ethyl group is regarded as $R^2$, and the two methyl groups bonded to the 1-position of the ethyl group are regarded as substituents.

With respect to the $C_2$ to $C_6$ alkenyl group, the carbon chain extending from the carbon atom which forms a nitrogen-carbon double bond in an iminoamide moiety (2-CONHN=C) of the pyridine, up to such a double bond as located at the furthest position therefrom, is regarded as $R^2$, and the $C_1$ to $C_4$ alkyl group bonded to $R^2$ is regarded as $X^a$.

With respect to the $C_2$ to $C_6$ alkynyl group, the carbon chain extending from the carbon atom which forms a nitrogen-carbon double bond in an iminoamide moiety (2-CONHN=C) of the pyridine, up to such a triple bond as located at the furthest position therefrom, is regarded as $R^2$, and the $C_1$ to $C_4$ alkyl group bonded to $R^2$ is regarded as $X^a$.

In the case where both the double and triple bonds are included in $R^2$, the carbon chain extending from the carbon atom which forms a nitrogen-carbon double bond in an iminoamide moiety (2-CONHN=C) of the pyridine, up to such a multiple bond as located at the furthest position therefrom, is regarded as $R^2$, and the $C_1$ to $C_4$ alkyl group bonded to $R^2$ is regarded as $X^a$.

The definitions of $R^3$ and the regularity between $R^3$ and $X^b$ are identical to those described above with respect to $R^2$ and $X^a$.

Specific examples of $R^2$ and $R^3$ may include the following substituents: a hydrogen atom; as the $C_1$ to $C_{10}$ alkyl group, a $C_1$ to $C_6$ alkyl group is preferred, and as the preferred $C_1$ to $C_6$ alkyl group, there may be exemplified methyl, ethyl, propyl, butyl or the like; as the $C_2$ to $C_6$ alkenyl group, there may be exemplified ethenyl, 1,3-butane-dienyl or the like; as the $C_2$ to $C_6$ alkynyl group, there may be exemplified ethynyl or the like; as the $C_3$ to $C_6$ cycloalkyl group, there may be exemplified cyclopropyl, cyclobutyl, cyclopentyl, cyclohexyl or the like; a phenyl group; and as the arylalkyl group (the alkyl moiety thereof has 1 to 3 carbon atoms), there may be exemplified phenylmethyl or the like.

$X^a$ and $X^b$ represent a halogen atom, a $C_1$ to $C_4$ alkoxy group, a $C_1$ to $C_4$ alkylthio group, a $C_1$ to $C_4$ alkyl group (which is not bonded to terminal positions of $R^2$ and $R^3$ when $R^2$ and $R^3$ are a $C_1$ to $C_{10}$ alkyl group), a $C_3$ to $C_6$ cycloalkyl group or a cyano group.

Specific examples of $X^a$ and $X^b$ may include the following substituents: as the halogen atom, there may be exemplified fluorine, chlorine, bromine or iodine; as the $C_1$ to $C_4$ alkyl group, there may be exemplified methyl, ethyl, (1-methyl)ethyl or the like; as the $C_3$ to $C_6$ cycloalkyl group, there may be exemplified cyclopropyl, cyclobutyl, cyclopentyl, cyclohexyl or the like; as the $C_1$ to $C_4$ alkoxy group, there may be exemplified methoxy, ethoxy, (1-methyl)ethoxy or the like; as the $C_1$ to $C_4$ alkylthio group, there may be exemplified methylthio, ethylthio, (1-methyl)ethylthio or the like; or a cyano group.

The integer $n^a$ is usually 0 (indicating that $R^2$ is unsubstituted with $X^a$) to 15, preferably 0 to 10, more preferably 0 to 7. The range of $n^a$ is explained in detail below according to the combination of $R^2$ and $X^a$.

In the case where $R^2$ is a $C_1$ to $C_{10}$ alkyl group, a $C_2$ to $C_6$ alkenyl group or a $C_2$ to $C_6$ alkynyl group, the range of $n^a$ varies depending upon the combination of $R^2$ and $X^a$ as is described below with respect to different $X^a$s.

In the case where $X^a$ is fluorine, $n^a$ is usually 1 to 15, preferably 1 to 10, more preferably 1 to 7.

In the case where $X^a$ is a halogen atom other than fluorine or an alkyl group, $n^a$ is usually 1 to 7, preferably 1 to 5, more preferably 1 to 3.

In the case where $X^a$ is a group other than halogen atom and alkyl group, $n^a$ is usually 1 to 3, preferably 1 to 2.

In the case where $R^2$ is a $C_3$ to $C_6$ cycloalkyl group, a phenyl group or a arylalkyl group, $n^a$ is in the range of usually 1 to 5, preferably 1 to 3 irrespective of kind of $X^a$.

The range of $n^b$ depending upon the combination of $R^3$ and $X^b$ is identical to the above-described range of $n^a$ depending upon the combination of $R^2$ and $X^a$.

Specific examples of $(R^2)X^a n^a$ may include the following groups.

In the case where $n^a$ is 0:
  Hydrogen atom;
  $C_1$ to $C_{10}$ alkyl groups such as methyl, ethyl, propyl, butyl, pentyl, hexyl, heptyl, octyl, nonyl, decyl or the like;
  $C_2$ to $C_6$ alkenyl groups such as ethenyl, 1,3-butane-dienyl or the like;
  $C_2$ to $C_6$ alkynyl groups such as ethynyl, 1-butene-3-ynyl, 2-pentene-4-ynyl or the like;
  $C_3$ to $C_6$ cycloalkyl groups such as cyclopropyl, cyclobutyl, cyclopentyl, cyclohexyl or the like;
  Phenyl group;
  Phenyl ($C_1$ to $C_3$ alkyl) groups (corresponding to arylalkyl groups whose alkyl moiety is $C_1$ to $C_3$ alkyl and whose aryl moiety is phenyl) such as phenylmethyl, phenylethyl, phenylpropyl or the like.

In the case where $X^a$ is alkyl and $n^a$ is 1 to 2:
  $C_3$ to $C_{12}$ alkyl groups such as 1-methylethyl, 1-methylpropyl, 1-methylbutyl, 2-methylpropyl, 2-methylbutyl, 1-ethylpropyl, 1,1-dimethylethyl, 1,1-dimethylpropyl or the like;
  $C_3$ to $C_9$ alkenyl groups such as 1-methylethenyl, 2-methylethenyl, 1,2-dimethylethenyl, 4-methyl-1,3-butane-dienyl, 4,4-dimethyl-1,3-butane-dienyl, 2,3-dimethyl-1,3-butane-dienyl or the like;
  $C_3$ to $C_9$ alkynyl groups such as 2-methylethynyl, 2-ethylethynyl, 4-methyl-1-butene-3-ynyl or the like;
  $C_4$ to $C_9$ cycloalkyl groups such as 2-methylcyclopropyl, 2,2-dimethylcyclopropyl, 2-methylcyclobutyl, 2-methylcyclopentyl, 2-methylcyclopentyl or the like;
  ($C_1$ to $C_4$ alkyl)phenyl groups such as 2-methylphenyl, 3-methylphenyl, 4-methylphenyl, 2-ethylphenyl, 3-ethylphenyl, 4-ethylphenyl, 3,4-dimethylphenyl, 2,4-dimethylphenyl or the like; and
  ($C_1$ to $C_4$ alkylphenyl) $C_1$ to $C_3$ alkyl groups such as (2-methylphenyl)methyl, (3-methylphenyl)methyl, (4-methylphenyl)methyl, 1-methyl(4-methylphenyl)methyl [identical to 1-(4-methylphenyl)ethyl], 2-methyl-2-(4-methylphenyl)ethyl, (2-ethylphenyl)methyl, (3-ethylphenyl)methyl, (4-ethylphenyl)methyl, (3,4-dimethylphenyl)methyl, (2,4-dimethylphenyl)methyl or the like.

In the case where $X^a$ is a halogen atom and $n^a$ is 1 to 7:
  Halogen-substituted $C_1$ to $C_{10}$ alkyl groups such as fluoromethyl, trifluoromethyl, difluoromethyl, 2-fluoroethyl, 4-fluorobutyl, chlorodifluoromethyl, bromodifluoromethyl, 2-bromo-2,2-difluoroethyl, 2,2,2-trifluoroethyl, 3,3,3-trifluoropropyl, 1,1,2,2,2-pentafluoroethyl, 1,1,2,2,3,3,3-heptafluoropropyl, trichloromethyl, chloromethyl, 2-chloroethyl, 3-chloropropyl, 2,2,2-trichloroethyl, 3,3,3-trichloropropyl, tribromomethyl, bromomethyl, 2-bromoethyl, 3-bromopropyl, iodofluoromethyl, 2-iodoethyl, 3-iodopropyl or the like;
  Halogen-substituted $C_2$ to $C_6$ alkenyl groups such as 1-chloroethenyl, 2,2-dichloroethenyl, 2-chloroethenyl, 4-chloro-1,3-butadienyl, 4,4-dichloro-1,3-butadienyl, 2,3-dichloro-1,3-butadienyl, 1-fluoroethenyl, 2,2-difluoroethenyl, 2-fluoroethenyl, 4-fluoro-1,3- butadienyl, 4,4-difluoro-1,3-butadienyl, 2,3-difluoro-1, 3-butadienyl, 1-bromoethenyl, 2,2-dibromoethenyl, 2-bromoethenyl, 4-bromo-1,3-butadienyl, 4,4-dibromo-1,3-butadienyl, 2,3-dibromo-1,3-butadienyl or the like;

Halogen-substituted $C_2$ to $C_6$ alkynyl groups such as 2-chloroethynyl, 4-chloro-1-butene-3-ynyl, 2-fluoroethynyl, 4-fluoro-1-butene-3-ynyl, 2-bromoethynyl, 4-bromo-1-butene-3-ynyl or the like;

Halogen-substituted $C_3$ to $C_6$ cycloalkyl groups such as 2-chlorocyclopropyl, 2,2-dichlorocyclopropyl, 2,2,3,3-tetrachlorocyclopropyl, 2-fluorocyclopropyl, 2,2-difluorocyclopropyl, 2,2,3,3-tetrafluorocyclopropyl or the like;

Halogen-substituted phenyl groups such as 2-chlorophenyl, 3-chlorophenyl, 4-chlorophenyl, 3,4-dichlorophenyl, 2,4-dichlorophenyl, 2-fluorophenyl, 3-fluorophenyl, 4-fluorophenyl, 3,4-difluorophenyl, 2,4-difluorophenyl, 2-bromophenyl, 3-bromophenyl, 4-bromophenyl, 3,4-dibromophenyl, 2,4-dibromophenyl, 2-iodophenyl, 3-iodophenyl or the like; and (Halogen-substituted phenyl) $C_1$ to $C_3$ alkyl groups such as (2-chlorophenyl)methyl, (3-chlorophenyl)methyl, (4-chlorophenyl)methyl, 2-(4-chlorophenyl)methyl, 2-(3-chlorophenyl)ethyl, 2-(4-chlorophenyl)ethyl, (2,4-dichlorophenyl)methyl, 2-(3-fluorophenyl)ethyl, 2-(4-fluorophenyl)ethyl, 1-(4-fluorophenyl)ethyl or the like.

In the case where $X^a$ is $C_1$ to $C_4$ alkoxy and $n^a$ is 1 to 2:

$C_1$ to $C_4$ alkoxy-substituted $C_1$ to $C_{10}$ alkyl groups such as methoxymethyl, ethoxymethyl, propoxymethyl, 2-(methoxy)ethyl, 1-(methoxy)ethyl, 1-(methoxy)propyl, 2-(ethoxy)ethyl, 3-(methoxy)propyl, 4-(methoxy)butyl, 2-(methoxy)propyl, 2-(ethoxy)propyl, 1-(ethoxy)propyl, 2,3-di(methoxy)propyl or the like;

$C_1$ to $C_4$ alkoxy-substituted $C_2$ to $C_6$ alkenyl groups such as 2-methoxyethenyl, 2-ethoxyethenyl or the like;

$C_1$ to $C_4$ alkoxy-substituted $C_2$ to $C_6$ alkynyl groups such as 2-methoxyethynyl or the like;

$C_1$ to $C_4$ alkoxy-substituted phenyl groups such as 2-methoxyphenyl, 3-methoxyphenyl, 4-methoxyphenyl, 2-ethoxyphenyl, 3-ethoxyphenyl, 4-ethoxyphenyl, 3,4-dimethoxyphenyl, 2,4-dimethoxyphenyl or the like; and ($C_1$ to $C_4$ alkoxy-substituted phenyl) $C_1$ to $C_3$ alkyl groups such as 2-(2-methoxyphenyl)ethyl, 2-(3-methoxyphenyl)ethyl, 2-(4-methoxyphenyl)ethyl, 1-(4-methoxyphenyl)ethyl, 2-(4-methoxyphenyl)propyl, (4-ethoxyphenyl)methyl, (3,4-dimethoxyphenyl)methyl, (2,4-dimethoxyphenyl)methyl or the like.

In the case where $X^a$ is alkylthio and $n^a$ is 1 to 2:

$C_1$ to $C_4$ alkylthio-substituted $C_1$ to $C_{10}$ alkyl groups such as (methylthio)methyl, (ethylthio)methyl, (propylthio)methyl, 2-(methylthio)ethyl, 2-(ethylthio)ethyl, 3-(methylthio)propyl, 4-(methylthio)butyl, 2-(methylthio)propyl, 2-(ethylthio)propyl, 1-(ethylthio)propyl, 2,3-di(methylthio)propyl or the like;

$C_1$ to $C_4$ alkylthio-substituted phenyl groups such as 2-(methylthio)phenyl, 3-(methylthio)phenyl, 4-(methylthio)phenyl or the like;

$C_1$ to $C_4$ alkylthio-substituted $C_2$ to $C_6$ alkenyl groups such as 2-(methylthio)ethenyl, 2-(ethylthio)ethenyl or the like;

$C_1$ to $C_4$ alkylthio-substituted $C_2$ to $C_6$ alkynyl groups such as 2-(methylthio)ethynyl or the like; and ($C_1$ to $C_4$ alkylthio-substituted phenyl) $C_1$ to $C_3$ alkyl groups such as [2-(methylthio)phenyl]methyl, [3-(methylthio)phenyl]methyl, [4-(methylthio)phenyl]methyl, [4-(ethylthio)phenyl]methyl or the like.

In the case where $X^a$ is cyano and $n^a$ is 1:

Cyano-substituted $C_1$ to $C_{10}$ alkyl groups such as cyanomethyl, 2-cyanoethyl, 3-cyanopropyl, 4-cyanobutyl or the like;

Cyano-substituted phenyl groups such as 2-cyanophenyl, 3-cyanophenyl, 4-cyanophenyl or the like;

(Cyano-substituted phenyl) $C_1$ to $C_3$ alkyl groups such as (2-cyanophenyl)methyl, (3-cyanophenyl)methyl, (4-cyanophenyl)methyl or the like.

In the case where $X^a$ is cycloalkyl and $n^a$ is 1:

$C_3$ to $C_6$ cycloalkyl-substituted $C_1$ to $C_{10}$ alkyl groups such as cyclopropylmethyl, cyclobutylmethyl, cyclopentylmethyl, cyclohexylmethyl, cyclopropylethyl or the like.

Specific examples of preferred $(R^2)X^a n^a$ may include a hydrogen atom, methyl, ethyl, propyl, butyl, ethenyl, 1,3-butadienyl, ethynyl, cyclopropyl, cyclohexyl, phenyl, 1-methylethyl, 2-methylbutyl, 1,1-dimethylethyl, 1-methylethenyl, 2-methylethenyl, 1,2-dimethylethenyl, 2-methylethynyl, 2-ethylethynyl, 4-methylphenyl, fluoromethyl, trifluoromethyl, difluoromethyl, 2-fluoroethyl, chlorodifluoromethyl, bromodifluoromethyl, 2-bromo-2,2-difluoroethyl, 2,2,2-trifluoroethyl, 3,3,3-trifluoropropyl, 1,1,2,2,2-pentafluoroethyl, 1,1,2,2,3,3,3-heptafluoropropyl, trichloromethyl, chloromethyl, 2-chloroethyl, 3-chloropropyl, 2,2,2-trichloroethyl, tribromomethyl, bromomethyl, 2-bromoethyl, 3-bromopropyl, 1-chloroethenyl, 2,2-dichloroethenyl, 2,2-difluoroethenyl, 2,2-dibromoethenyl, 2,2-dichlorocyclopropyl, 4-fluorophenyl, 4-chlorophenyl, 2,4-difluorophenyl, methoxymethyl, ethoxymethyl, 2-(methoxy)ethyl, 2-methoxyethenyl, 2-ethoxyethenyl, 4-methoxyphenyl, (methylthio)methyl, (ethylthio)methyl, 2-(methylthio)ethyl, 2-(ethylthio)ethyl, 4-(methylthio)phenyl, cyanomethyl, 2-cyanoethyl, 4-cyanophenyl and cyclopropylmethyl.

Specific examples of more preferred $(R^2)X^a n^a$ may include a hydrogen atom, ethenyl, ethynyl, phenyl, 2-methylbutyl, 1,1-dimethylethyl, 1-methylethenyl, 2-methylethenyl, 1,2-dimethylethenyl, 2-methylethynyl, trifluoromethyl, chlorodifluoromethyl, bromodifluoromethyl, 1,1,2,2,2-pentafluoroethyl, 1,1,2,2,3,3,3-heptafluoropropyl, trichloromethyl, chloromethyl, 4-fluorophenyl, 4-chlorophenyl, 2,4-difluorophenyl, methoxymethyl, ethoxymethyl, (methylthio)methyl, (ethylthio)methyl, 2-(methylthio)ethyl, cyanomethyl, 4-cyanophenyl and cyclopropyl.

Specific examples of still more preferred $(R^2)X^a n^a$ may include halogenated alkyl groups such as trifluoromethyl, chlorodifluoromethyl, 1,1,2,2,2-pentafluoroethyl, 1,1,2,2,3,3,3-heptafluoropropyl, trichloromethyl, chloromethyl or the like.

Specific examples of $(R^3)X^b n^b$ are identical to those of $(R^2)X^a n^a$ as described above.

With respect to the preferred combinations of $(R^2)X^a n^a$ and $(R^3)X^b n^b$, when $(R^2)X^a n^a$ is any one of the above substituents, it is preferred that $(R^3)X^b n^b$ is a hydrogen atom, a $C_1$ to $C_3$ alkyl group or a $C_1$ to $C_3$ haloalkyl group.

Specific examples of $(R^3)X^b n^b$ may include a hydrogen atom, methyl, ethyl, propyl, butyl, 1-methylethyl, fluoromethyl, trifluoromethyl, chlorodifluoromethyl, bromodifluoromethyl, 2,2,2-trifluoroethyl, 1,1,2,2,2- pentafluoroethyl, 1,1,2,2,3,3,3-heptafluoropropyl, trichloromethyl, chloromethyl, tribromomethyl and bromomethyl.

Specific examples of preferred $(R^3)X^b n^b$ may include a hydrogen atom, methyl and trifluoromethyl. Especially, it is more preferred that $(R^3)X^b n^b$ is a hydrogen atom.

When both of $R^2$ and $R^3$ are alkyl chains, $R^2$ and $R^3$ may be directly bonded with each other, or $R^2$ and $R^3$ may be bonded to each other through an oxygen atom, a sulfur atom or a nitrogen atom (the nitrogen atom may be alkylated with $C_1$ to $C_4$ alkyl groups), so as to form a ring together with the carbon atom contained in an imino moiety of 2-CONHN=C of the compound (I).

As such ring or cyclic compounds, when these compounds are expressed as a group bonded to the nitrogen atom of the imino moiety of 2-CONHN=C of the compound (I), there may be exemplified those groups forming a ring by direct carbon—carbon bond between $R^2$ and $R^3$, such as cyclobutylidene, cyclopentylidene, cyclohexylidene, cycloheptylidene or the like; those groups forming a ring by bonding carbon atoms of $R^2$ and $R^3$ with each other through an oxygen atom, such as 2-methyl-3-tetrahydrofurylidene, tetrahydro-4-pyranylidene or the like; those groups forming a ring by bonding carbon atoms of $R^2$ and $R^3$ with each other through a sulfur atom, such as tetrahydro-4-thiopyranylidene or the like; or those groups forming a ring by bonding carbon atoms of $R^2$ and $R^3$ with each other through a nitrogen atom (which may be alkylated with a $C_1$ to $C_4$ alkyl group, i.e., such a nitrogen atom to which a hydrogen atom or $C_1$ to $C_4$ alkyl group is bonded) such as 1-methyl-4-piperidylidene, 4-piperidylidene or the like.

Specific examples of Y of the present compound (I) may include $C_1$ to $C_4$ haloalkyl groups such as trifluoromethyl or the like; $C_1$ to $C_4$ alkyl groups such as methyl, ethyl, (1-methyl)ethyl or the like; $C_1$ to $C_4$ alkoxy groups such as methoxy, ethoxy, (1-methyl)ethoxy or the like; $C_1$ to $C_4$ haloalkoxy groups such as trifluoromethoxy, difluoromethoxy or the like; $C_1$ to $C_4$ alkylthio groups such as methylthio, ethylthio, (1-methyl)ethylthio or the like; $C_1$ to $C_4$ haloalkylthio groups such as trifluoromethylthio, difluoromethylthio or the like; or halogen atoms such as fluorine, chlorine, bromine or the like.

Among the above groups, as preferred Y, there may be exemplified trifluoromethyl, methyl, methoxy, trifluoromethoxy, difluoromethoxy, methylthio, trifluoromethylthio, chlorine and bromine.

Examples of more preferred Y may include trifluoromethyl, trifluoromethoxy, trifluoromethylthio and chlorine.

The integer p is usually 0 (which means unsubstituted condition) to 5, preferably 0 to 3. It is more preferred that p is 1 and Y is bonded to the 3-position.

As the present compounds (I) obtained by the combination of the above preferred substituents and integers, there may be exemplified the following compounds as shown in Tables 1 to 7 below.

TABLE 1

| Compound No. | R$^1$ a) | R$^2$ X$^a$n$^a$ b) | R$^3$ X$^b$n$^b$ b) | Yp d) |
|---|---|---|---|---|
| I-1 | 4-OCH$_3$ | CH$_2$CH$_2$CH$_3$ - | H | 3-CF$_3$ |
| I-2 | 4-OCH$_3$ | CH$_2$CH$_3$ — | H | 3-CF$_3$ |

TABLE 1-continued

| Compound No. | R$^1$ a) | R$^2$ X$^a$n$^a$ b) | R$^3$ X$^b$n$^b$ b) | Yp d) |
|---|---|---|---|---|
| I-3 | 4-OCH$_3$ | CH$_3$ — | H | 3-CF$_3$ |
| I-4 | 4-OCH$_3$ | CHCH$_3$ 1-CH$_3$ | H — | 3-CF$_3$ |
| I-5 | 4-OCH$_3$ | C 1,1,1-F$_3$ | H — | 3-CF$_3$ |
| I-6 | 4-OCH$_3$ | CC 1,1,2,2,2-F$_5$ | H — | 3-CF$_3$ |
| I-7 | 4-OCH$_3$ | CH$_2$ 1-Cl | H — | 3-CF$_3$ |
| I-8 | 4-OCH$_3$ | CH$_2$ 1-F | H — | 3-CF$_3$ |
| I-9 | 4-OCH$_3$ | CH$_2$ 1-Br | H — | 3-CF$_3$ |
| I-10 | 4-OCH$_3$ | H — | H — | 3-CF$_3$ |

TABLE 2

| Compound No. | R$^1$ a) | R$^2$ X$^a$n$^a$ b) | R$^3$ X$^b$n$^b$ b) | Yp d) |
|---|---|---|---|---|
| I-11 | 4-OCH$_3$ | CH$_2$ 1-OCH$_3$ | H — | 3-CF$_3$ |
| I-12 | 4-OCH$_3$ | CH$_2$ 1-SCH$_3$ | H — | 3-CF$_3$ |
| I-13 | 4-OCH$_3$ | cyclopropyl — | H — | 3-CF$_3$ |
| I-14 | 4-OCH$_3$ | cyclopropyl — | CH$_3$ — | 3-CF$_3$ |
| I-15 | 4-OCH$_3$ | Ch$_2$ 1-CN | H — | 3-CF$_3$ |
| I-16 | 4-OCH$_3$ | CH$_3$ — | CH$_3$ — | 3-CF$_3$ |
| I-17 | 4-OCH$_3$ | CC 1,1,2,2,2-F$_5$ | H — | 3-OCF$_3$ |
| I-18 | 4-OCH$_3$ | CC 1,1,2,2,2-F$_5$ | H — | 3-SCF$_3$ |
| I-19 | 4-OCH$_3$ | CC 1,1,2,2,2-F$_5$ | H — | 3-OCHF$_2$ |
| I-20 | 4-OCH$_3$ | CC 1,1,2,2,2-F$_5$ | H — | 3-CH$_3$ |

TABLE 3

| Compound No. | R$^1$ a) | R$^2$ X$^a$n$^a$ b) | R$^3$ X$^b$n$^b$ b) | Yp d) |
|---|---|---|---|---|
| I-21 | 4-OCH$_3$ | CC 1,1,2,2,2-F$_5$ | H — | 3-OCH$_3$ |
| I-22 | 4-OCH$_3$ | CC 1,1,2,2,2-F$_5$ | H — | 3-Cl |
| I-23 | 4-OCH$_3$ | CC 1,1,2,2,2-F$_5$ | H — | 4-Cl |
| I-24 | 4-OCH$_3$ | CC 1,1,2,2,2-F$_5$ | H — | 2-Cl |
| I-25 | 4-OCH$_3$ | CH$_2$CH$_3$ — | CH$_3$ — | 3-CF$_3$ |
| I-26 | 4-OCH$_3$ | CH$_2$CH$_3$ — | CH$_2$CH$_3$ — | 3-CF$_3$ |
| I-27 | 4-OCH$_3$ | CH$_2$ 1-OCH$_3$ | CH$_3$ — | 3-CF$_3$ |
| I-28 | 4-OCH$_3$ | CH$_2$ 1-SCH$_3$ | CH$_3$ — | 3-CF$_3$ |

TABLE 3-continued

| Compound No. | R¹ a) | R² $X^an^a$ b) | R³ $X^bn^b$ b) | Yp d) |
|---|---|---|---|---|
| I-29 | 4-OCH₃ | CH₂CH₂ 2-SCH₃ | CH₃ — | 3-CF₃ |
| I-30 | 4-OCH₃ | C 1,1,1-F₃ | CH₃ — | 3-CF₃ |

TABLE 1

| Compound No. | R¹ a) | R² $X^an^a$ b) | R³ $X^bn^b$ b) | Yp d) |
|---|---|---|---|---|
| I-31 | 4-OCH₃ | C 1,1,1-F₃ | C 1,1,1-F₃ | 3-CF₃ |
| I-32 | 4-OCH₃ | Ph — | H — | 3-CF₃ |
| I-33 | 4-OCH₃ | Ph 2,4-F₂ | H — | 3-CF₃ |
| I-34 | 4-OCH₃ | Ph 4-CN | H — | 3-CF₃ |
| I-35 | 4-OCH₃ | Ph — | CH₃ — | 3-CF₃ |
| I-36 | 4-OCH₃ | CH₂Ph — | H — | 3-CF₃ |
| I-37 | 4-OCH₃ | CH = CH 2-CH₃ | H — | 3-CF₃ |
| I-38 | 4-OCH₃ | cycloheyxl — | CH₃ — | 3-OCH₃ |
| I-39 | 4-SCH₃ | CC 1,1,2,2,2-F₅ | H — | 3-CF₃ |
| I-40 | 4-(NCH₃)₂ | CC 1,1,2,2,2-F₅ | H — | 3-CF₃ |

TABLE 1

| Compound No. | R¹ a) | R² $X^an^a$ b) | R³ $X^bn^b$ b) | Yp d) |
|---|---|---|---|---|
| I-41 | 4-NHCH₃ | CC 1,1,2,2,2-F₅ | H — | 3-CF₃ |
| I-42 | 4-NHCH₂CH₃ | CC 1,1,2,2,2-F₅ | H — | 3-CF₃ |
| I-43 | 4-NHCH₂CH₃ | CH₃ — | CH₃ — | 3-CF₃ |
| I-44 | 4-N(CH₂Ph)CH₃ | CC 1,1,2,2,2-F₅ | H — | 3-CF₃ |
| I-45 | 4-N(CH₂Ph)CH₂CH₃ | CH₃ 1,1,2,2,2-F₅ | H — | 3-CF₃ |
| I-46 | 5-OCH₃ | CC 1,1,2,2,2-F₅ | H — | 3-CF₃ |
| I-47 | 3-Cl | CC 1,1,2,2,2-F₅ | H — | 3-CF₃ |
| I-48 | — | CC 1,1,2,2,2-F₅ | H — | 3-CF₃ |
| I-49 | — | C 1,1,1-Cl₃ | H — | 3-CF₃ |
| I-50 | — | C 1-Cl-1,1,-F₂ | H — | 3-CF₃ |

TABLE 6

| Compound No. | R¹ a) | R² $X^an^a$ b) | R³ $X^bn^b$ b) | Yp d) |
|---|---|---|---|---|
| I-51 | 4-CH₃ | CC 1,1,2,2,2-F₅ | H — | 3-CF₃ |
| I-52 | — | C 1,1,1-F₃ | C 1,1,1-F₃ | 3-CF₃ |
| I-53 | 4-OCH₃ | C = C 2-CH₃ | H — | 3-CF₃ |
| I-54 | 4-OCH₃ | CCC 1,1,2,2,3,3,3-F₇ | H — | 3-CF₃ |

TABLE 7

| Compound No. | R¹ a) | R² $X^an^a$ c) | R³ $X^bn^b$ c) | Yp d) |
|---|---|---|---|---|
| I-100 | 4-OCH₃ | CH₂CH₂CH₂CH₂ | | 3-CF₃ |
| I-101 | 4-SCH₃ | CH₂CH₂CH₂CH₂ | | 3-CF₃ |
| I-102 | — | CH₂CH₂CH₂CH₂ | | 3-CF₃ |
| I-103 | 4-OCH₃ | CH₂CH₂CH₂CH₂CH₂ | | 3-CF₃ |
| I-104 | 4-OCH₃ | CH₂CH₂OCH₂CH₂ | | 3-CF₃ |
| I-105 | 4-OCH₃ | CH₂CH₂SCH₂CH₂ | | 3-CF₃ |
| I-106 | 4-OCH₃ | CH₂CH₂N(CH₃)CH₂CH₂ | | 3-CF₃ |

Note:

a): $R^1$ represents a substituent group bonded to the pyridine ring. For example, "4-OCH₃" of the compound (I-1) means that "OCH₃" is bonded to the carbon atom located at the 4-position of the pyridine ring.

b): 1) In the case where $R^2$ is a chain hydrocarbon compound:

As to "CHCH₃" of the compound No. (I-4), it shows that the carbon atom thereof which lacks in hydrogen atoms, is bonded to the carbon atom of the imino moiety of 2-CONHN=C of the pyridine, and the same carbon atom is also bonded to $X^an^a$. Here, the $X^an^a$ in Tables are explained (similarly applicable to $X^bn^b$) The symbol: "–" means an unsubstituted condition ($n^a$=0). Also, in the case where $R^2$ has any substituents, the number prefixed to the hyphen (en dash) represents the bonding position of each substituent. In the above Tables, since $R^2X^an^a$ is shown in the form of a group bonded to the carbon atom of the imino moiety of 2-CONHN=C of the pyridine as in the present specification, the bonding position of $X^an^a$ is indicated assuming that the carbon atom of $R^2$ which is bonded to the carbon atom of the imino moiety is located at the 1-position. Namely, "1-CH₃" means that "CH₃" is bonded to the 1-position carbon atom of CHCH₃ which is bonded to the carbon atom of the imino moiety of 2-CONHN=C of the pyridine.

"CC" of the compound No. (I-6) represent that the carbon atom which lacks in bonding number, is bonded to the carbon atom of the imino moiety of 2-CONHN=C of the pyridine, and further five fluorine atoms are bonded to the "CC". Thus, if two or more carbon atoms which lacks in bonding number, are present, the position of the leftmost carbon atom is regarded as the 1-position.

In the case where $R^2$ is composed of carbon and hydrogen, $R^2$ is shown as if the carbon atom which is bonded to the carbon atom of the imino moiety of 2-CONHN=C of the pyridine and further to $X^an^a$ would lack in bonding number.

2) In the case where $R^2$ is phenyl:

In the case where $R^2$ is represented by Ph and the Ph has substituents thereon, the number prefixed to the hyphen (en dash) represents the bonding position of each substituent, and the name of each substituent ($X^a$), and the number ($n^a$) of the substituents if two or more bonding positions exist, are suffixed to the hyphen (en dash). The above expression method of $X^a n^a$ is also applicable to that of $X^b n^b$.

The symbol: "–" means an unsubstituted condition ($n^a$=0). Also, in the case where Ph has any substituents, the number prefixed to the hyphen (en dash) represents the bonding position of each substituent to the benzene ring. The bonding position is indicated assuming that the carbon atom of the phenyl group which is bonded to the carbon atom of the imino moiety of 2-CONHN=C of the pyridine, is located at the 1-position. Namely, in the compound No. (I-33), it is indicated that $R^2$ is Ph, and one fluorine atom is bonded to each of the 2- and 4- position carbon atoms of the phenyl group assuming that the carbon atom of Ph which is bonded to the carbon atom of the imino moiety of 2-CONHN=C of the pyridine, is located at the 1-position.

The expression method of $R^2$ is identically applicable to that of $R^3$.

c): In the case where $R^2$ and $R^3$ are alkyl chains, and further in the case where $R^2$ and $R^3$ may be directly bonded with each other to form a ring or $R^2$ and $R^3$ may be bonded to each other through an oxygen atom, a sulfur atom or a nitrogen atom (the nitrogen atom may be alkylated with $C_1$ to $C_4$ alkyl groups) to form a ring, the whole structure of $R^2 X^a n^a$ and $R^3 X^b n^b$ is indicated. In this case, the hyphen (en dash) prefixed to the carbon atom which is bonded to the carbon atom of the imino moiety of 2-CONHN=C of the pyridine, represents the bonding position. In the compound (I-100), it is indicated that the alkyl chains are directly bonded with each other to form a 5-membered ring. In addition, "O" of the compound (I-104) indicates that the alkyl chains of $R^2$ and $R^3$ are bonded with each other through an oxygen atom to form a ring; "S" of the compound (I-105) indicates that the alkyl chains are bonded with each other through a sulfur atom to form a ring; and "N(CH3)" of the compound (I-106) indicates that the alkyl chains are bonded with each other through a nitrogen atom to form a ring.

d): "Yp" represents a substituent bonded to the phenoxy ring. In the case where the substituent bonded to the phenoxy ring is present, the number prefixed to the hyphen (en dash) indicates the bonding position. In this case, the bonding position is determined assuming that the carbon atom of the phenoxy ring which is bonded to the carbon atom of the pyridine through an oxygen atom, is located at the 1-position. In the compound (I-1), "3-$CF_3$" indicates that $CF_3$ is bonded to the 3-position carbon atom of the phenoxy ring.

Next, the process for producing the present compound (I) is explained.

In the production process according to the second aspect of the present invention, as the solvents used, there may be usually exemplified aromatic hydrocarbons such as benzene, toluene, xylene, methyl naphthalene or the like; aliphatic hydrocarbons such as petroleum ethers, pentane, hexane, heptane, methyl cyclohexane or the like; halogenated hydrocarbons such as methylene chloride, chloroform, carbon tetrachloride, chlorobenzene or the like; amides such as dimethyl formamide, dimethyl acetamide, N-methyl-2-pyrrolidinone or the like; ethers such as diethyl ether, dimethoxy ethane, diisopropyl ether, tetrahydrofuran, diethylene glycol dimethyl ether (DIGLYME), dioxane or the like; or alcohols such as methanol, ethanol or the like.

As other solvents usable in the present invention, there may be exemplified water, acetic acid, carbon disulfide, acetonitrile, ethyl acetate, pyridine, dimethyl sulfoxide, hexamethyl phosphoric triamide or the like. These solvents may be used singly or in the form of a mixture of any two or more thereof. Individual reaction steps of the production process according to the present invention can be advantageously carried out in the presence of either a solvent or a mixed solvent. In addition, there may be used a solvent composition containing solvents which are inhibited from forming a uniform layer when mixed with each other. In the case where such a solvent composition is used, a phase transfer catalyst, for example, ordinarily used quaternary ammonium salts or crown ethers may be added to the reaction system.

Next, the production process according to the second aspect of the present invention, is explained in detail below.

The compound (I) of the present invention can be produced by adding a 6-phenoxy picolinic acid hydrazide derivative represented by the general formula (II) to a carbonyl group of aldehydes or ketones represented by the general formula (III) and then subjecting the obtained addition product to dehydration. The above reaction is represented by the following reaction formula:

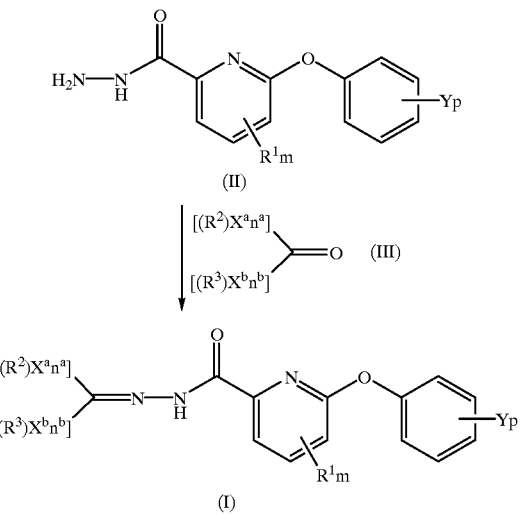

wherein $R^1$, $R^2$, $R^3$, Y, $X^a$, $X^b$, m, $n^a$, $n^b$ and p have the same definitions as described above.

The above reaction may be usually carried out by mixing the compounds (III) and (II) together in a solvent or in a reaction system containing an excessive amount of the compound (III) capable of acting as a solvent. Further, sine the present reaction is an addition dehydration reaction between a nitrogen atom of the hydrazide and a carbonyl group of the aldehydes or ketones, the reaction may sometimes proceed without any catalyst. However, in other cases, it might be preferable to conduct the reaction using acid as a catalyst or using an organic acid such as acetic acid as a solvent. Alternatively, the reaction may also be carried out using a solvent such as benzene for azeotropic dehydration. The compounds (III) may be used in an excessive amount based on that of the compound (II) because the use of such an excessive amount of the compound (III) tends to promote the reaction. However, the amount of the compound (III) used is usually 0.5 to 1,000 moles, preferably 0.8 to 500 moles based on one mole of the compound (II).

The reaction temperature is usually 0 to 200° C., preferably 10 to 150° C.

The reaction time is usually several minutes to several days.

As the acidic compounds used in the above reaction, there may be exemplified the following compounds.

As the acids, there may be usually exemplified inorganic acids such as hydrochloric acid, hydrobromic acid, hydriodic acid, perchloric acid, sulfuric acid or the like; or organic acids such as formic acid, acetic acid, p-toluene sulfonic acid or the like. These acids may be used singly or in the form of a mixture of any two or more thereof.

As the above compound (III), there may be used commercially available products or those compounds which can be produced by conventionally known techniques. Further, such commercially available products sold in the form of stable hydrates or acetals of the compound (III), or the stable hydrates or acetals which are produced by conventionally known techniques, may also be used as the compound (III) by removing the protecting groups therefrom.

As the compound (III), there may be exemplified the following aldehydes (including preparation reagents thereof). Examples of such aldehydes as the compound (III) in which at least one of $R^2$ and $R^3$ is a hydrogen atom, may include:

formaldehyde;

unsubstituted alkanecarboxaldehydes such as acetaldehyde, n-propionaldehyde, n-butyraldehyde, 2-methyl pronionaldehyde or the like;

halogen-substituted alkanecarboxaldehydes such as chloroacetaldehyde, bromoacetaldehyde, chloral, bromal, chlorodifluoroacetaldehyde hydrate, trifluoroacetaldehyde hydrate, 2,2,3,3,3-pentafluoropropionaldehyde hydrate, 2,2,3,3,4,4,4-heptafluorobutyraldehyde hydrate or the like;

alkoxy-substituted alkanecarboxaldehydes such as methoxy acetaldehyde, 3-methoxy propionaldehyde dimethyl acetal, 3-methoxy butyraldehyde dimethyl acetal or the like;

alkylthio-substituted alkanecarboxaldehydes such as 3-(methylthio)propionaldehyde, (methylthio) acetaldehyde dimethyl acetal or the like;

cyano-substituted alkanecarboxaldehydes such as cyanoacetaldehyde dimethyl acetal, 3-cyanopropionaldehyde dimethyl acetal or the like;

alkenecarboxaldehydes such as crotonaldehyde, 3-methyl-2-butenal or the like;

alkynecarboxaldehydes such as 2-butyne-1-al diethyl acetal or the like;

cycloalkanecarboxaldehydes such as cyclopropane carboxaldehyde, cyclohexane carboxaldehyde or the like;

alkyl-substituted benzaldehyde such as 2-methyl benzaldehyde, 3-methyl benzaldehyde, 4-methyl benzaldehyde or the like;

halogen-substituted benzaldehydes such as 2-chlorobenzaldehyde, 3-bromobenzaldehyde, 4-fluorobenzaldehyde 2,4-difluorobenzaldehyde or the like;

alkoxy-substituted benzaldehydes such as 2-methoxy benzaldehyde, 3-methoxy benzaldehyde, 4-ethoxy benzaldehyde or the like;

alkylthio-substituted benzaldehydes such as 4-(methylthio)benzaldehyde or the like;

cyano-substituted benzaldehydes such as 2-cyanobenzaldehyde, 3-cyanobenzaldehyde, 4-cyanobenzaldehyde or the like; or arylalkanecarboxaldehydes such as phenyl acetaldehyde, 2-phenyl propionaldehyde or the like.

These aldehydes themselves can be used as the compound (III) as they are. Further, there may also be used such compounds which can be produced by using known methods such as oxidation reaction of primary alcohols or alkyl groups, reduction reaction of carboxylic acid derivatives (such as carboxylic acid, acid halides, acid amides or esters) or the like.

Next, the ketones (including preparation reagents thereof) as the compound (III) are exemplified below. Examples of such ketones as the compound (III) in which neither $R^2$ nor $R^3$ is a hydrogen atom, may include:

dialkyl ketones such as acetone, 2-propanone, 3-butanone, 3-pentanone, 3-methyl-2-pentanone or the like;

halogen-substituted dialkyl ketones such as 1,1,1-trifluoro-2-propanone, hexafluoro-2-propanone, 1-chloro-1,1,3,3,3-pentafluoro-2-propanone, 1,1,1,2,2,3,3-heptafluoro-4-pentanone, 3-bromo-1,1,1-trifluoro-2-propanone, 3-chloro-1,1,1-trifluoro-2-propanone or the like;

alkoxy-substituted dialkyl ketones such as 1-methoxy-2-propanone or the like;

alkylthio-substituted dialkyl ketones such as 3-methylthio-2-butanone or the like;

cycloalkyl(alkyl) ketones such as cyclopropyl methyl ketone or the like;

dicycloalkyl ketones such as dicyclopropyl ketone, dicyclohexyl ketone or the like;

alkenyl(alkyl) ketones such as 3-butene-2-one, 4-methoxy-3-butene-2-one, 4-ethoxy-1,1,1-trifluoro-3-butene-2-one or the like;

alkynyl(alkyl) ketones such as 3-butyne-2-one or the like;

various phenyl(alkyl) ketones such as acetophenone, p-(methylthio) acetophenone, m-(methoxy) acetophenone, o-methyl acetophenone, p-chloro acetophenone, p-cyano acetophenone, chlorodifluoro acetophenone, cyclopropyl phenyl ketone, cyclopropyl p-fluorophenyl ketone, cyclohexyl phenyl ketone or the like;

various benzophenones such as benzophenone, p-(methoxy) benzophenone, m-methyl benzophenone or the like;

aralkyl(alkyl) ketones such as phenyl acetone, benzyl acetone or the like; or various cyclic ketones such as cyclobutanone, cyclopentanone, cyclohexanone, cycloheptanone, 2-methyl tetrahydrofuran-3-one, tetrahydro-4H-pyran-4-one, 4-oxothiane or the like.

These ketones themselves can be used as the compound (III) as they are. Further, there may also be used such compounds which can be produced by using known methods such as oxidation reaction of secondary alcohols, substitution reaction of carboxylic acid derivatives (such as carboxylic acid, acid halides, acid amides or esters) using organic metal reagents, hydrolysis of dihalides or the like The above compound (II) can be produced by the following two methods.

(1) In the method (1), the compound (II) can be obtained by substituting an leaving group W of the compound represented by the general formula (IV) with a nitrogen atom of hydrazine.

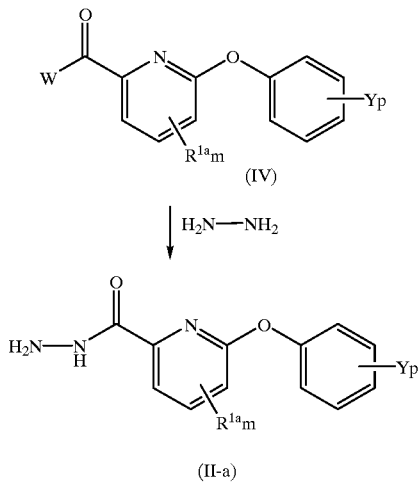

(II-a)

wherein $R^{1a}$ is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ dialkylamino group or a ($C_1$ to $C_4$ alkyl)($C_7$ to $C_8$ aralkyl) amino group; W is a halogen atom, a lower alkoxy group or a hydroxyl group; and Y, m and p have the same definitions as described above.

(2) In the method (2), the compound (II) can be obtained by substituting an leaving group W of the compound represented by the general formula (IV) with the 2-position nitrogen atom of 1,1-dibenzyl hydrazine to produce the compound represented by the general formula (V), and then subjecting the obtained compound (V) to hydrogenolysis.

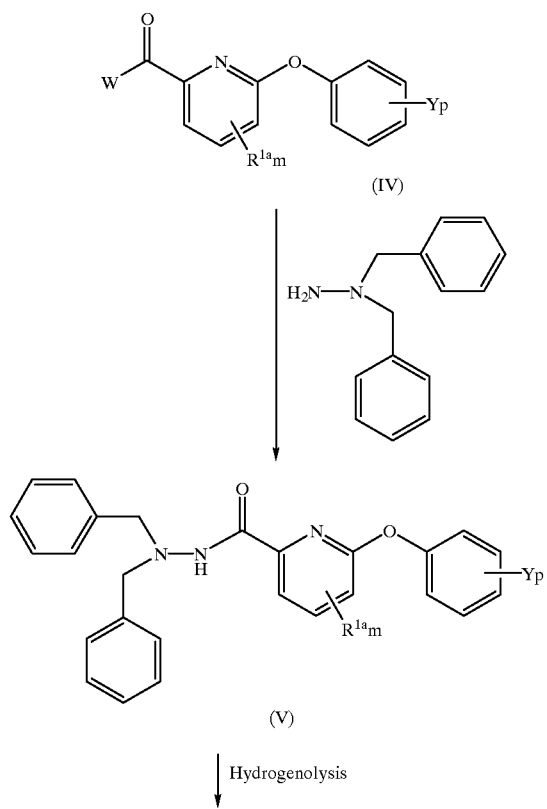

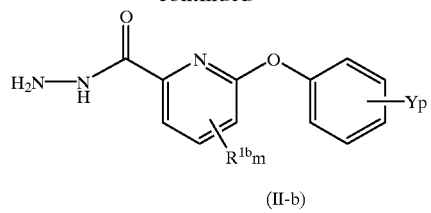

(II-b)

wherein $R^{1b}$ is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ dialkylamino group or a ($C_1$ to $C_4$ alkyl) ($C_7$ to $C_8$ aralkyl) amino group (excluding those groups whose aralkyl is phenylmethyl susceptible to hydrogenolysis); W is a lower alkoxy group, a halogen atom or a hydroxyl group; and $R^{1a}$, Y, m and p have the same definitions as described above.

The production methods of the compound (II) are described in more detail below.

(1) The production method (1) of the compound (II) may be usually carried out in an organic solvent. Since the $NH_2$ group of hydrazide of the obtained compound (II-a) tends to be reacted with the compound (IV), it is preferred that hydrazine be used in an excessive amount based on the compound (IV). The amount of hydrazine used is usually 1.0 to 1,000 moles, preferably 2.0 to 100 moles based on one mole of the compound (IV). In the case where acid salts such as sulfates or hydrochlorides are used as a hydrazine source, a base such as triethylamine may be present together therewith in not less than one equivalent amount based on the acid in order to facilitate the isolation of hydrazine therefrom. As the leaving groups, there may be used lower alkoxy groups such as methoxy or ethoxy, halogen atoms such as chlorine or bromine, a hydroxy group or the like. When the lower alkoxy group is used as the leaving group, it is possible to reduce the amount of by-product compounds formed by bonding two molecules of the compound (IV) to hydrazine, because such compounds (IV) containing the lower alkyl group as the leaving group have a less reactivity than those containing the halogen atom as the leaving group. Further, the lower alkoxy group can exhibit a higher leaving property than that of the hydroxyl group. Therefore, the lower alkoxy group is considered to be a more preferable leaving group.

The reaction temperature is usually 0 to 200° C., preferably 10 to 100° C.

The reaction time is usually several minutes to several days.

(2) In the production method (2) of the compound (II), the production of the compound (V) is first explained. The reaction for producing the compound (V) from the compound (IV) may be usually carried out in an organic solvent. As the leaving group, there may be used halogen atoms such as chlorine or bromine, lower alkoxy groups such as methoxy or ethoxy, or the like. The compounds (IV) containing a halogen atom as the leaving group show a higher reactivity than those containing a lower alkoxy group as the leaving group. Therefore, as the leaving group, the use of halogen atoms is preferred. Among them, the use of a chlorine atom is more preferred.

Even though the halogen atom is used as the leaving group, it is unnecessary to use 1,1-dibenzyl hydrazine in a highly excessive amount unlike in the method (1). However, since hydrogen halide is produced during the reaction, 1,1-dibenzyl hydrazine is preferably added to the reaction system in such an amount which is larger by not less than one equivalent than that of the compound (IV), in order to capture the hydrogen halide produced. The amount of 1,1-dibenzyl hydrazine used is usually 2.0 to 10.0 moles, preferably 2.0 to 5.0 moles based on one mole of the compound (IV).

Alternatively, in order to remove the hydrogen halide produced, a base such as triethyl amine may co-exist in the reaction solution instead of adding the excessive amount of 1,1-dibenzyl hydrazine thereto. In this case, the amount of 1,1-dibenzyl hydrazine used is usually 1.0 to 5.0 moles, preferably 1.0 to 3.0 moles based on one mole of the compound (IV). Also, in the case where acid salts such as sulfates or hydrochlorides are used as a source of 1,1-dibenzyl hydrazine, a base such as triethyl amine may co-exist in not less than one equivalent amount based on the acid in order to facilitate the isolation of 1,1-dibenzyl hydrazine therefrom.

The reaction temperature is usually 0 to 200° C., preferably 10 to 100° C.

The reaction time is usually several minutes to several days.

In the above method, in the case where lower alkoxy group or hydroxyl group is used as the leaving group, no hydrogen halide is produced during the reaction. Therefore, it is unnecessary to add 1,1-dibenzyl hydrazine in more than one equivalent amount based on that of the compound (IV) or add triethyl amine to the reaction system. The amount of 1,1-dibenzyl hydrazine used is usually 1.0 to 10.0 moles, preferably 1.0 to 5.0 moles based on one mole of the compound (IV).

The reaction temperature is usually 0 to 250° C., preferably 10 to 180° C.

The reaction time is usually several minutes to several days.

Next, the method of producing the compound (II-b) by hydrogenolysis of the compound (V) is explained below. The hydrogenolysis reaction of the compound (V) may be usually carried out in a solvent. As the hydrogenation catalyst, there may be usually exemplified metals such as platinum, palladium, nickel or the like whose catalytic activity is enhanced by increasing a surface area thereof, or those obtained by supporting these metals on a carrier such as activated carbon, carbon, barium carbonate, alumina or the like. Among these catalysts, the use of palladium carbon, Raney nickel or the like is preferred. The above reaction may proceed without a reaction accelerator. When such a reaction accelerator is used, as the suitable reaction accelerator, there may be exemplified acids such as hydrochloric acid, perchloric acid, acetic acid or the like. The above reaction may be usually carried out at a temperature of from room temperature to 100° C. for a period of 30 minutes to several days.

Next, the method for producing the compound (IV) used as raw material in the above reaction is explained.

In the case where the leaving group W of the compound (IV) is a halogen atom:

Such a compound (IV) can be produced by halogenating 6-phenoxy picolinic acid (VI) using a halogenation reagent such as thionyl chloride, phosphoryl chloride, phosphorus pentachloride, phosphorus trichloride, phosphoryl bromide or the like. The above reaction is represented by the following reaction formula:

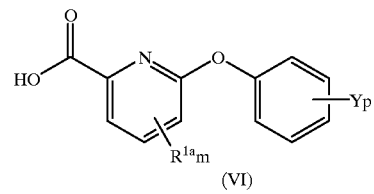

wherein Wa is a halogen atom; and $R^{1a}$, Y, m and p have the same definitions as described above.

The halogenation reaction may be carried out in a solvent such as benzene, toluene or the like which is inert to the obtained acid halide (IV-a), at a temperature of usually 0 to 250° C., preferably 30 to 150° C.

The amount of the halogenation reagent used is usually 0.3 to 10 moles, preferably 1 to 5 moles based on one mole of 6-phenoxy picolinic acid (VI). In the above reaction, it is preferable to use a reaction accelerator such as dimethyl formamide or the like.

The reaction time is usually several minutes to several days.

In the case where the leaving group W of the compound (IV) is a lower alkoxy group:

Such a compound (IV) can be produced by esterifying the 6-phenoxy picolinic acid halide (IV-a) with lower alcohol. The above reaction is represented by the following reaction formula:

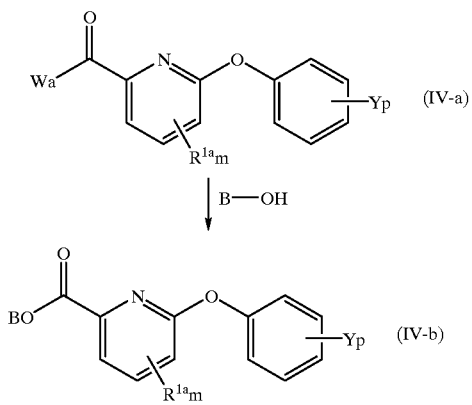

wherein B is a lower alkyl group; and $R^{1a}$, Y, m and p have the same definitions as described above.

The above esterification reaction may be carried out in a solvent such as benzene, toluene or the like which is inert to the acid halide, or by using the raw lower alcohol as a solvent, at a temperature of usually 0° C. to the reflux point, preferably from room temperature to the reflux point.

The amount of the lower alcohol used is usually 0.5 to 1,000 moles, preferably 1 to 100 moles based on one mole of the compound (IV-a). In addition, in order to capture hydrogen halide produced in the course of the esterification reaction, the use of a base such as triethyl amine is preferred.

The reaction time is usually several minutes to several days.

Some of the 6-phenoxy picolinic acid compounds (compound (IV)) used in the present invention have been described in Japanese Patent Application Laid-Open (KOKAI) No. 4-217959(1992) [for example, compounds (VI) wherein m is 0; and Yp is 3-$CF_3$, or the like].

Although the compound (VI) may be produced by the method described in Japanese Patent Application Laid-Open (KOKAI) No. 4-217959(1992), the following production methods of the compound (VI) are also exmplified.

The first production method of the compound (VI) is explained below. A 2-halogeno-6-phenoxy pyridine derivative (hereinafter referred to merely as compound (VIII)) is metallated to obtain a 2-(metal-substituted)-6-phenoxy pyridine derivative represented by the general formula (VII) (hereinafter referred to merely as compound (VII)). Thereafter, the compound (VII) is reacted with carbon dioxide, and thereafter the resultant product is proton-substituted, thereby producing the compound (VI). The above reaction is represented by the following reaction formula:

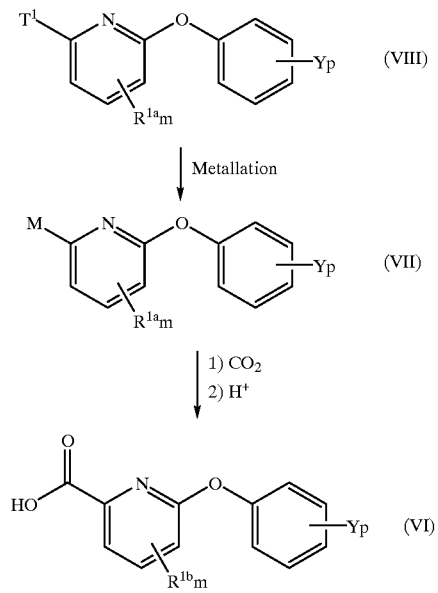

wherein $T^1$ is a halogen atom; M is alkali metal, alkali earth metal-Q wherein Q is a halogen atom, or ½(Cu-alkali metal); and $R^{1a}$, Y, m and p have the same definitions as described above.

As metallizing reagents for the metallation of the compound (VIII), there may be usually exemplified organic alkali metal compounds such as butyl lithium, methyl lithium or phenyl lithium; alkali metals such as lithium, sodium or potassium; alkali earth metals such as magnesium; or the like. In addition, as the other metallizing reagents, there may be exemplified organic copper compounds produced by reacting organic alkali metal compounds prepared from the above metallizing reagents or Grignard reagents with monovalent copper salts, or the like.

The compound (VII) can be produced by treating the compound (VIII) with the above metallizing reagent. The temperature used for the treatment with the metallizing reagent is usually −100° C. to 100° C., preferably −80° C. to 80° C.

The reaction time is usually several minutes to several hours.

The compound (VI) can be produced by reacting the thus obtained compound (VII) with carbon dioxide and then subjecting the resultant product to proton-substitution. The proton-substitution may be carried out by treating the obtained reaction solution with an aqueous acid solution. As the acids used, there may be exemplified inorganic acids such as hydrochloric acid, hydrobromic acid, hydriodic acid, perchloric acid, sulfuric acid or the like; or organic acids such as formic acid, acetic acid, p-toluene sulfonic acid or the like. These acids may be used singly or in the form of a mixture of any two or more thereof.

As the solvents used in the production of the compound (VI), there may be exemplified those inert to the organic metal compounds, e.g., aliphatic hydrocarbons such as petroleum ethers, pentane, hexane, heptane, methyl cyclohexane or the like; ethers such as diethyl ether, dimethoxy ethane, diisopropyl ether, tetrahydrofuran, diethylene glycol dimethyl ether (DIGLIM), dioxane or the like; or aromatic hydrocarbons such as benzene, toluene, xylene, methyl naphthalene or the like. These solvents may be used singly or in the form of a mixture of any two or more thereof.

The above compound (VIII) can be produced by reacting a 2,6-dihalogenopyridine derivative (hereinafter referred to merely as "compound (IX)") with substituted or unsubstituted phenol represented by the general formula (X) (hereinafter referred to merely as "compound (X)") usually in an organic solvent in the presence of a base. The reaction temperature is usually 20 to 200° C., preferably 60 to 180° C. The reaction time is several minutes to several hours. The above reaction is represented by the following reaction formula:

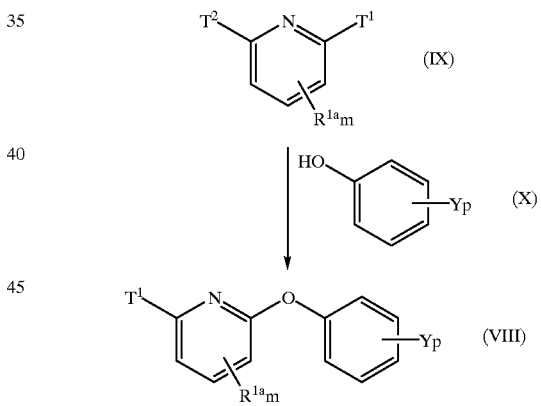

wherein $T^1$ and $T^2$ are halogen atoms and may be the same or different; and $R^{1a}$, Y, m and p have the same definitions as described above.

The above reaction and the syntheses of the below-described compounds represented by the general formulae (XI) and (XIII) are nucleophilic substitution reactions to the carbon atom of pyridine ring and, therefore, preferably carried out in the presence of a base. As the base, there may be exemplified:

alkali metals such as lithium, sodium, potassium or the like;

alkali earth metals such as magnesium or the like;

alkali metal alkoxides such as sodium methoxide, sodium ethoxide, potassium t-butoxide or the like;

alkali metal hydrides such as sodium hydride, potassium hydride or the like;

alkali metal carbonates such as potassium carbonate, sodium carbonate or the like;

alkali earth metal carbonates such as calcium carbonate, barium carbonate or the like;

alkali earth metal hydrides such as calcium hydride or the like;

alkali metal hydroxides such as sodium hydroxide, potassium hydroxide or the like;

alkali earth metal hydroxides such as calcium hydroxide, magnesium hydroxide or the like;

alkali earth metal oxides such as magnesium oxide, calcium oxide or the like;

organic alkali metal compounds such as methyl lithium, ethyl lithium, n-butyl lithium, phenyl lithium or the like;

organic Grignard reagents such as methyl magnesium iodide, ethyl magnesium bromide, n-butyl magnesium bromide or the like;

organic copper compounds prepared by reacting organic alkali metal compounds or Grignard reagents with monovalent copper salts; or alkali metal amides such as lithium diisopropyl amide or the like.

The compound (IX) as the raw material of the above reaction can be produced by the following method.

First, 2,6-dihalogeno-substituted pyridine can be produced as follows. For instance, 2,6-dibromo-4-methyl pyridine [corresponding to the compound (IX) wherein $T^1$ and $T^2$ are Br and $R^{1a}m$ is 4-$CH_3$] as one example of 2,6-dihalogeno-4-substituted pyridine, can be produced by substituting a hydroxyl group of 2-bromo-6-hydroxy-4-methyl pyridine with a halogen atom, as described in Japanese Patent Application Laid-Open (KOKAI) No. 6-40813 (1994). As the halogen atom, there may be exemplified chlorine, bromine, iodine or the like.

Also, 2,6-dihalogeno-4-(alkoxy, haloalkoxy, alkylthio, alkylamino or dialkylamino) pyridine [corresponding to the compound (IX) wherein $T^1$ and $T^2$ are halogen atoms and $R^{1a}m$ is 4-(alkoxy, haloalkoxy, alkylthio, alkylamino or dialkylamino)] can be produced by subjecting the nitro group of corresponding 2,6-dihalogeno-4-nitro pyridine to nucleophilic substitution under a basic condition, as described in Japanese Patent Application Laid-Open (KOKAI) Nos. 6-40813(1994) or 8-269055(1996). The dialkylamino compound and the aralkyl(alkyl)amino compound may be produced by alkylation or aralkylation of the above alkylamino compound.

As the 3- or 5-substituted compounds (IX), there may be used those produced by conventional techniques. As to the compounds (IX) having different 3- and 5-substituents, since the compound (VIII) produced by the phenoxylation reaction is obtained in the form of a mixture therewith, the mixture may be used as the compound (IX) as it is, or the compound (IX) may be used after separating from the mixture.

Also, since the 4-nitro group is relatively easily substituted, the 4-nitro compound can be suitably used for the production of 4-substituted compounds [especially, 4-(alkylamino, dialkylamino or aralkyl(alkyl)amino) compounds].

As the above phenols (X), there may be used commercially available products or those compounds which can be produced by conventional techniques. Examples of the phenols may include phenol, 3-chlorophenol, 3-methylphenol, 3-methoxyphenol, 3-(methylthio) phenol, 3-(trifluoromethyl) phenol, 3-(trifluoromethoxy) phenol, 3-(difluoromethoxy) phenol, 3-(trifluoromethylthio) phenol or the like.

Next, the second production method of the compound (VI) is explained. In the second production method, the compound (VI) can be produced by hydrolyzing a 2-cyano-6-phenoxy pyridine derivative represented by the general formula (XI) (hereinafter referred to merely as "compound (XI)"). The above reaction is represented by the following reaction formula:

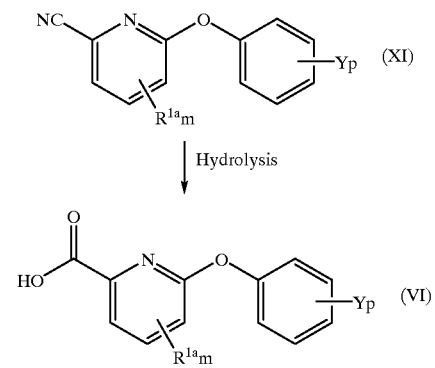

wherein $R^{1a}$, Y, m and p have the same definitions as described above.

The above hydrolysis can be carried out in either acid or basic conditions. In the case where the hydrolysis is carried out under acid conditions, as the catalyst therefor, there may be usually used inorganic acids such as hydrochloric acid, hydrobromic acid, sulfuric acid or the like. As the solvents used under such acid conditions, there may be usually exemplified water or water containing an organic aid such as acetic acid or the like. In the case where the hydrolysis is carried out under basic conditions, as the base, there may be usually used alkali metal bases such as sodium hydroxide, potassium hydroxide or the like. As the solvent used under such basic conditions, there may be usually exemplified water or water containing alcohols or the like.

The reaction temperature of the hydrolysis is in the range of usually from 20° C. to the reflux point, preferably from 50° C to the reflux point. The reaction time of the hydrolysis is usually several minutes to several hours.

The above compound (XI) can be produced by reacting a 2-cyano-6-halogeno pyridine derivative represented by the general formula (XII) (hereinafter referred to merely as "compound (XII)") with the compound (X) usually in an organic solvent under basic conditions. The reaction temperature is usually 20° C. to 200° C., preferably 60° C. to 180° C. The reaction time is usually several minutes to several days. The above reaction is represented by the following reaction formula:

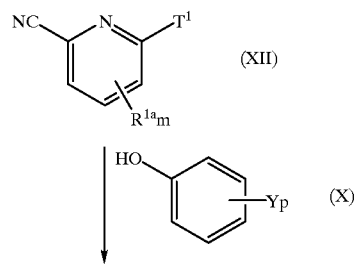

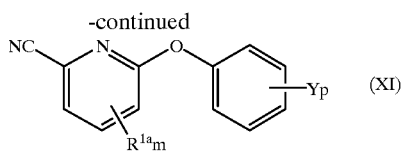

wherein $T^1$, $R^{1a}$, Y, m and p have the same definitions as described above.

The above compound (XII) can be produced as follows.

First, 2-cyano-6-chloro-4-methyl pyridine [corresponding to such a compound (XII), wherein $T^1$ is chlorine and $R^{1a}$m is 4-CH$_3$] as the 4-substituted compound can be produced by substituting 2-bromo-6-chloro-4-methyl pyridine with copper cyanide, as described in International Patent Publication W094/08991.

Also, 2-cyano-4,6-dichloro pyridine [corresponding to such a compound (XII) wherein $T^1$ is chlorine and $R^{1a}$m is 4-Cl] can be produced by chlorinating 2-cyano pyridine, as described in British Patent No. 1,301,724. By subjecting the obtained compound to nucleophilic substitution under basic conditions, there can be obtained 2-cyano-6-chloro-4-(alkoxy, haloalkoxy, alkylamino or alkylthio) pyridine [corresponding to such a compound (XII) wherein $T^1$ is chlorine and $R^{1a}$m is 4-(alkoxy, haloalkoxy, amino, alkylamino or alkylthio), and such a compound containing a amino group bonded to the 4-position of the pyridine ring]. Further, the 4-dialkylamino compound or the 4-alkylaralkylamino compound can be produced by reacting the 4-alkylamino compound with alkyl halide or aralkyl halide under basic conditions. Similarly, by using the 4-amino compound, there can be obtained the 4-alkylamino compound, the 4-dialkylamino compound, the 4-aralkylamino compound and the 1-alkylaralkylamino compound.

The 2-cyano-3,6-dichloro pyridine [corresponding to such a compound (XII) wherein $T^1$ is chlorine and $R^{1a}$m is 3-Cl] as the 3-substituted compound is described in USSR Patent No. 1,728,241 or U.S. Pat. No. 740,935.

Next, the third production method of the compound (VI) is explained. In the third production method, the compound (VI) can be produced by hydrolyzing a 6-phenoxy picolinic acid ester derivative represented by the general formula (XIII) (hereinafter referred to merely as "compound (XIII)"). The above reaction is represented by the following reaction formula:

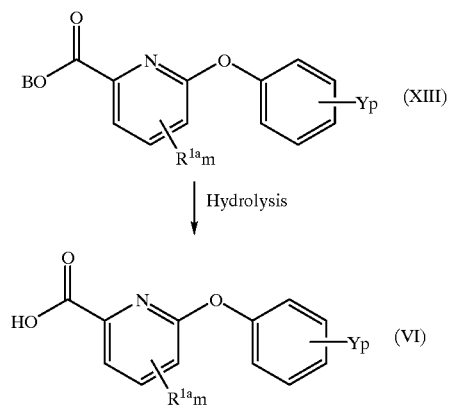

wherein B is a lower alkyl group; and $R^{1a}$, Y, m and p have the same definitions as described above.

The above hydrolysis can be carried out in either acid or basic conditions. In the case where the hydrolysis is carried out under acid conditions, as the catalyst used therefor, there may be usually used inorganic acids such as hydrochloric acid, hydrobromic acid, sulfuric acid or the like. As the solvent used under such acid conditions, there may be usually exemplified water or water containing an organic acid such as acetic acid or the like. In the case where the hydrolysis is carried out under basic conditions, as the base, there may be usually used alkali metal bases such as sodium hydroxide, potassium hydroxide or the like. As the solvent used under such basic conditions, there may be usually exemplified water or water containing alcohols or the like.

The reaction temperature of the hydrolysis is in the range of usually from 20° C. to the reflux point, preferably from 50° C. to the reflux point. The reaction time of the hydrolysis is usually several minutes to several hours.

The above compound (XIII) can be produced by reacting a 6-phenoxy picolinic acid ester derivative represented by the general formula (XIV) (hereinafter referred to merely as "compound (XIV)") with the compound (X) usually in an organic solvent under basic conditions. The reaction temperature is in the range of usually 20° C. to 200° C., preferably 60° C. to 180° C. The reaction time is usually several minutes to several days. The above reaction is represented by the following reaction formula:

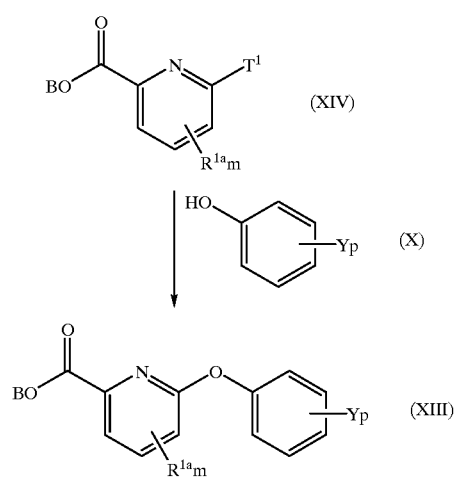

wherein $T^1$, B, $R^{1a}$, Y, m and p have the same definitions as described above.

The above compound (XIV) can be produced as follows.

First, the production of the 4-substituted compound (XIV) is explained. The 4-chlorinated compound (XIV) can be synthesized by reacting N-methyl pyridone acid with thionyl chloride to produce 4,6-dichloro picolinic acid chloride, and then reacting the obtained 4,6-dichloro picolinic acid chloride with lower alkanol to produce 4,6-dichloro picolinic acid lower alkyl ester [corresponding to such a compound (XIV) wherein $T^1$ is chlorine and $R^{1a}$m is 4-Cl], as described in J. Org. Chem., 23, 1030(1958).

Alternatively, the 4,6-dichloro picolinic acid lower alkyl ester [corresponding to the compound (XIV) wherein $T^1$ is chlorine and $R^{1a}$m is 4-Cl] can be produced by halogenating 4,6-dichloro picolinic acid obtained by oxidation of 4,6-dichloro-2-methyl pyridine, using a halogenation reagent such as thionyl chloride to produce an acid halide, and then reacting the obtained acid halide with lower alkanol. By subjecting the thus obtained compound to nucleophilic substitution under basic conditions, there can be obtained 6-chloro-4-(alkoxy, haloalkoxy, amino, alkylamino or alkylthio) picolinic acid lower alkyl ester [corresponding to such a compound (XIV) wherein $T^1$ is chlorine and $R^{1a}m$ is 4-(alkoxy, haloalkoxy, alkylamino or alkylthio), and a compound (XIV) containing a amino group bonded to the 4-position of the pyridine ring]. Further, the 4-dialkylamino compound or the 4-alkylaralkylamino compound can be produced by reacting the 4-alkylamino group [as $R^{1a}m$ of the compound (XIV)] with alkyl halide or aralkyl halide under basic conditions. Similarly, by using the 4-amino compound, there can be obtained the 4-alkylamino compound, the 4-dialkylamino compound, the 4-aralkylamino compound and the 4-alkylaralkylamino compound.

Next, the production of the 3-substituted compound (XIV) is explained. The substituted picolinic acid can be produced by hydrolyzing substituted 2-trihalomethyl pyridine obtained by halogenating the 2-methyl group of substituted 2-picoline. The above method includes the halogenation reaction and, therefore, is suitable for the production of such compounds (XIV) containing a halogen atom as $R^{1a}$. For example, 3,6-dichloro picolinic acid obtained by this method is described in U.S. Pat. No. 3,317,549. By halogenating the picolinic acid to produce an acid halide and then reacting the obtained acid halide with lower alkanol, it is possible to obtain such a compound (XIV) wherein $T^1$ is chlorine and $R^{1a}m$ is 3-Cl.

Also, as to the compound (XIV) having a $C_1$ to $C_4$ alkoxy group bonded to the 5-position thereof, 5-alkoxy-6-halogeno picolinic acid can be synthesized by alkylating a 5-hydroxyl group of 6-halogeno-5-hydroxy picoline with $C_1$ to $C_4$ alkyl to convert the hydroxyl group into an ether bond, and then oxidizing the 2-methyl group of the thus obtained 5-alkoxy-6-halogeno-2-picoline into a carboxyl group. 6-bromo-5-methoxy picolinic acid as an example of the 5-alkoxy compounds (XIV) has been described in Pharmazie 38(9), 591(1983). By esterifying the above compound with lower alkyl, there can be obtained such a compound (XIV) wherein $T^1$ is chlorine and $R^{1a}m$ is 5-$OCH_3$.

In the production of the substituted picolinic acid by oxidation reaction, in the case where the picolinic acid has a substituent bonded to the 4-position thereof, such a compound can be preferably produced by first producing 2-pyridine methanol from 2-picoline N-oxides and then oxidizing the hydroxymethyl group of 2-pyridine methanol into the carboxyl group, rather than by directly oxidizing the 2-methyl group of pyridine ring into the carboxyl group. For instance, 4-methoxy-6-chloro picolinic acid can be synthesized by oxidizing a hydroxymethyl group of 4-methoxy-6-chloro-2-pyridine methanol. When the obtained picolinic acid is esterified, there can be obtained such a compound (XIV) wherein $T^1$ is chlorine and $R^{1a}m$ is 4-$OCH_3$.

The reaction temperature and the reaction time described in respective reactions, can be varied according to necessary reaction operations, for example, the reaction temperature can be shifted to either lower or higher temperature side and the reaction time can be prolonged, unless these changes adversely affect the yield of aimed products.

The present compound (I) may be used as a herbicide. However, the compound (I) may be usually formulated together with preparation auxiliaries or adjuvants into various forms such as dusting powder, water-dispersible powder, granules or emulsion. In this case, the obtained preparation may contain at least one kind of the compound (I) according to the present invention in an amount of usually 0.1 to 95% by weight, preferably 0.5 to 90% by weight, more preferably 2 to 70% by weight based on the weight of the preparation.

Carriers, diluents and surfactants used as the preparation auxiliaries or adjuvants may be exemplified as follows.

Examples of solid carriers may usually include talc, kaolin, bentonite, diatomaceous earth (diatomite), white carbon, clay or the like. Examples of liquid diluents may usually include water, xylene, toluene, chlorobenzene, cyclohexane, cyclohexanone, dimethyl sulfoxide, dimethyl formamide, alcohols or the like.

Various surfactants may be selectively used according to the applications. As emulsions, there may be usually exemplified polyoxyethylene alkylaryl ether, polyoxyethylene alkyl ether, polyoxyethylene sorbitan monolaurate or the like. As dispersants, there may be usually exemplified lignin sulfonate, dibutylnaphthalene sulfonate or the like. As wetting agents, there may be usually exemplified alkyl sulfonate, alkylphenyl sulfonate or the like.

The above-mentioned preparations are used without diluting, or are used as a preparation diluted with a diluent such as water to the predetermined concentration. In the case where the preparations are diluted upon use, the concentration of the present compound (I) in the preparations is usually in the range of 0.001 to 1.0%. The amount of the present compound (I) used is usually 0.001 to 10 kg, preferably 0.01 to 5 kg per one hectare (ha). The concentrations and amounts of the preparations used may be varied according to types of preparations used, the time, method or place of use, kinds of crops to be treated or the like and, therefore, increased or decreased concentrations or amounts may also be used without being limited to the above-specified range. Further, the present compound (I) may be used in combination with other effective ingredients, for example, fungicide, insecticide, miticide, herbicide or the like.

BEST MODE FOR CARRYING OUT THE INVENTION

The present invention will be described in more detail below by examples, but these examples are not intended to limit the scope of the present invention.

EXAMPLE 1

Production of 4-methoxy-6-[3-(trifluoromethyl) phenoxy] picolinic acid, (n-propylidene) hydrazide (compound No. I-2)

4-methoxy-6-[3-(trifluoromethyl)phenoxy] picolinic acid hydrazide (0.5 g, 0.0015 mol) was mixed with propionaldehyde (0.27 g, 0.0015×3.1 mol), and further with a mixed solution of diethyl ether and chloroform and a small amount of concentrated hydrochloric acid. The resultant solution was heated and refluxed for about 8 hours. The obtained reaction solution was concentrated and then purified by silica gel column chromatography (eluting solution: ethyl acetate/hexane), thereby obtaining an aimed product.

Yield weight: 0.41 g; yield percentage: 73%; solid; melting point: 154 to 155° C.; $^1$H-NMR (250 MHz, $CDCl_3$, δ): 1.00(1.8H, t, J=7.3 Hz), 1.10(1.2H, t, J=7.3 Hz), 1.69(1.2H, dq, J=5.4, 7.3 Hz), 2.38(0.8H, dq, J=5.4,7.3 Hz), 3.94(1.2H, s), 3.95(1.8H, s), 6.55(0.4H, d, J=2.4 Hz), 6.63(0.6H, d, J=2.4 Hz), 6.77(0.6H, t, J=5.4 Hz), 7.0–7.7(5.4H, complex), 10.00(0.4H, s), 10.21(0.6H, s)

EXAMPLE 2

Production of 4-methoxy-6-[3-(trifluoromethyl) phenoxy picolinic acid, (2-chloroethylidene) hydrazide (compound No. I-7)

4-methoxy-6-[3-(trifluoromethyl)phenoxy] picolinic acid hydrazide (0.25 g, 0.00076 mol) was mixed with chloroacetaldehyde [0.13 ml (ca. 40% aqueous solution), 0.00076×1.05 mol] and ethanol (about 5 ml). The resultant solution was stirred at room temperature for about 4 hours. The obtained reaction solution was concentrated and then purified by silica gel column chromatography (eluting solution: ethyl acetate/hexane), thereby obtaining an aimed product.

Yield weight: 0.26 g; yield percentage: 88%; solid; melting point: 102 to 103° C.; $^1$H-NMR (60 MHz, CDCl$_3$, δ): 3.86(3H, s), 4.16(2H, d, J=6 Hz), 6.50(1H, d, J=2 Hz), 7.0–7.7(6H, complex), 10.14(1H, s)

EXAMPLE 3

Production of 4-methoxy-6-[3-(trifluoromethyl) phenoxy] picolinic acid, (2-cyanoethylidene) hydrazide (compound No. I-15)

3,3-dimethoxy propionitrile (0.35 g, 0.0015×2 mol) was dissolved in a 2N aqueous hydrochloric acid solution (about 10 ml). The obtained solution was stirred at a temperature of about 50 to 60° C. for about one hour. The solution was further mixed with benzene (about 10 ml) and 4-methoxy-6-[3-(trifluoromethyl)phenoxy] picolinic acid hydrazide (0.50 g, 0.0015 mol), and then the resultant mixture was stirred at that temperature for about one hour. The obtained reaction solution was distributed in ethyl acetate-water The organic phase separated from the solution was successively washed with saturated sodium bicarbonate water and with saturated brine, and then dried with anhydrous sodium sulfate. Thereafter, the resultant solution was concentrated and then purified by silica gel column chromatography (eluting solution: ethyl acetate/hexane), thereby obtaining an aimed product.

Yield weight: 0.51 g; yield percentage: 88%; solid; melting point: 98 to 100° C.; $^1$H-NMR (60 MHz, CDCl$_3$, δ): 3.39(2H, d, J=4.5 Hz), 3.83(3H, s), 6.45(1H, d, J=2 Hz), 6.9–7.6(6H, complex), 9.70(1H, s)

EXAMPLE 4

Production of 4-methoxy-6-[3-(trifluoromethyl) phenoxy] picolinic acid, (i-propylidene) hydrazide (compound No. I-16)

Acetone (10 ml, 0.0015×91 mol) was added to 4-methoxy-6-[3-(trifluoromethyl)phenoxy] picolinic acid hydrazide (0.5 g, 0.0015 mol). The resultant mixture was stirred at room temperature for about one hours. The obtained reaction solution was concentrated, thereby obtaining an aimed product.

Yield weight: 0.54 g; yield percentage: 96%; solid; melting point: 134 to 136° C.; $^1$H-NMR (60 MHz, CDCl$_3$, δ): 1.43(3H, s), 2.00(3H, s), 3.86(3H, s), 6.55(2H, d, J=2 Hz), 7.0–7.8(5H, complex), 9.92(1H, s)

EXAMPLE 5

Production of 4-methoxy-6-[3-(trifluoromethyl) phenoxy picolinic acid, [1-(trifluoromethyl)-2,2,2-trifluoroethylidene] hydrazide (compound No. I-31)

4-methoxy-6-[3-(trifluoromethyl)phenoxy] picolinic acid hydrazide (0.5 g, 0.0015 mol) and hexafluoroacetone trihydrate (1.00 g, 0.0015×3 mol) were suspended in an aqueous benzene/4N hydrochloric acid solution (about 10 ml/about 5 ml), and the obtained suspension was stirred at about 60° C. for about one hour. Thereafter, the suspension was mixed with benzene and refluxed for about 8 hour using a water separator. The obtained reaction solution was distributed in ethyl acetate-saturated sodium bicarbonate water, and the organic phase separated from the solution was washed with saturated brine, dried with anhydrous sodium sulfate and then concentrated. The obtained concentrated solution was mixed with toluene (about 5 ml) and refluxed for about 5 hours. The obtained reaction solution was distributed in ethyl acetate-saturated sodium bicarbonate water, and the organic phase separated from the solution was washed with saturated brine, dried with anhydrous sodium sulfate and then concentrated. The obtained concentrated solution was purified by silica gel column chromatography (eluting solution: ethyl acetate/hexane), thereby obtaining an aimed product.

Yield weight: 0.089 g; yield percentage: 12%; solid; melting point: 84 to 86° C.; $^1$H-NMR (60 MHz, CDCl$_3$, δ): 3.88(3H, s), 6.61(1H, d, J=2 Hz), 6.9–7.6(5H, complex), 11.27(1H, s)

EXAMPLE 6

Production of 4-methoxy-6-[3-(trifluoromethyl) phenoxy] picolinic acid, (1-phenylethylidene) hydrazide (compound No. I-35)

4-methoxy-6-[3-(trifluoromethyl)phenoxy] picolinic acid hydrazide (0.30 g, 0.00092 mol) was mixed with acetophenone (0.11 ml, 0.00092×1.0 mol) and p-toluene sulfonic acid monohydrate (0.06 g, 0.00092×0.34 mol), and further with. benzene (about 20 ml). The obtained mixture was refluxed for about 3 hours so as to pass through a molecular sieve 4A. The obtained reaction solution was distributed in ethyl acetate-water, and the organic phase separated from the solution was washed with saturated brine, dried with anhydrous sodium sulfate and then concentrated. The obtained concentrated solution was purified by silica gel column chromatography (eluting solution: ethyl acetate/hexane), thereby obtaining an aimed product.

Yield weight: 0.28 g; yield percentage: 71%; solid; melting point: 181 to 182° C.; $^1$H-NMR (60 MHz, CDCl$_3$, δ): 1.78(3H, s), 3.87(3H, s), 6.54(1H, d, J=2 Hz), 7.1–8.0(10H, complex), 10.22(1H, s)

EXAMPLE 7

Production of 4-dimethylamino-6-[3-(trifluoromethyl)phenoxy] picolinic acid, (2,2,3,3,3-pentafluoropropylidene] hydrazide (compound No. I-40)

4-dimethylamino-6-[3-(trifluoromethyl)phenoxy] picolinic acid hydrazide (0.30 g, 0.00088 mol) was mixed with 2,2,3,3,3-pentafluoropropionaldehyde monohydrate (0.29 g, 0.00088×2.0 mol) and benzene, and further with a small amount of concentrated hydrochloric acid. The obtained mixture was refluxed and dehydrated for about 8 hours using a water separator. The obtained reaction solution was distributed in ethyl acetate-saturated sodium bicarbonate water, and the organic phase separated from the solution was washed with saturated brine, dried with anhydrous sodium sulfate and then concentrated. The obtained concentrated solution was purified by silica gel column chromatography (eluting solution: ethyl acetate/hexane), thereby obtaining an aimed product.

Yield weight: 0.28 g; yield percentage: 68%; solid; melting point: 108 to 109° C.; $^1$H-NMR (60 MHz, CDCl$_3$, δ): 3.02(6H, s), 6.12(1H, d, J=2 Hz), 6.9–7.6(5H, complex), 8.20(1H, d, J=7 Hz), 10.65(1H, s)

EXAMPLE 8

Production of 4-ethylamino-6-[3-(trifluoromethyl) phenoxy] picolinic acid, (2,2,3,3,3-pentafluoropropylidene] hydrazide (compound No. I-42)

4-ethylamino-6-[3-(trifluoromethyl)phenoxy] picolinic acid hydrazide (0.30 g, 0.00088 mol) was mixed with 2,2,3,3,3-pentafluoropropionaldehyde monohydrate (0.29 g, 0.00088×2.0 mol) and benzene, and further with a small amount of concentrated hydrochloric acid. The obtained mixture was refluxed and dehydrated for about 8 hours using a water separator. The obtained reaction solution was distributed in ethyl acetate-saturated sodium bicarbonate water, and the organic phase separated from the solution was washed with saturated brine, dried with anhydrous sodium sulfate and then concentrated. The obtained concentrated solution was purified by silica gel column chromatography (eluting solution: ethyl acetate/hexane), thereby obtaining an aimed product.

Yield weight: 0.25 g; yield percentage: 60%; solid; melting point: 101 to 102° C.; $^1$H-NMR (60 MHz, CDCl$_3$, δ): 1.26(3H, t, J=7 Hz), 3.18(2H, dq, J=5, 7 Hz), 5.00(1H, t, J=5 Hz), 6.07(1H, d, J=2 Hz), 6.8–7.6(5H, complex), 7.99(1H, t, J=7 Hz), 10.67(1H, s)

EXAMPLE 9

Production of 3-chloro-6-[3-(trifluoromethyl) phenoxy] picolinic acid, (2,2.3,3,3-pentafluoropropylidene] hydrazide (compound No. I-47)

3-chloro-6-[3-(trifluoromethyl)phenoxy]-2-picolinic acid hydrazide (0.4 g, 0.0012 mol) was dissolved in 5 ml of acetic acid. The obtained solution was mixed with 2,2,3,3,3-pentafluoropropionaldehyde monohydrate (0.199 g, 0.0012×1.0 mol), and the resultant mixture was stirred at 80° C. for 3 hours. A chilled water was poured into the obtained reaction solution which was then distributed in ethyl acetate-water. The organic phase separated from the solution was washed with water and then dried with anhydrous sodium sulfate. After distilling off the solvent from the dried product, the obtained distillation residues were purified by silica gel column chromatography (eluting solution: ethyl acetate/hexane), thereby obtaining an aimed product.

Yield weight: 0.25 g; yield percentage: 45%; solid; melting point: 130 to 131° C.; $^1$H-NMR (60 MHz, CDCl$_3$, δ): 7.05(1H, d, J=8 Hz), 7.1–7.6(4H, complex), 7.78(1H, d, J=8 Hz), 8.40(1H, t, J=6 Hz), 10.0–10.3(1H, br)

EXAMPLE 10

Production of 6-[3-(trifluoromethyl)phenoxy] picolinic acid, (2,2,2-trichloroethylidene] hydrazide (compound No. I-49)

6-[3-(trifluoromethyl)phenoxy] picolinic acid hydrazide (0.15 g, 0.000505 mol) was mixed with trichloroacetaldehyde (0.22 g, 0.000505×3.0 mol) and benzene (about 20 ml). The obtained mixture was refluxed for about 3 hours. The obtained reaction solution was distributed in ethyl acetate-saturated sodium bicarbonate water, and the organic phase separated from the solution was washed with saturated brine, dried with anhydrous sodium sulfate and then concentrated. The obtained concentrated solution was purified by silica gel column chromatography (eluting solution: ethyl acetate/hexane), thereby obtaining an aimed product.

Yield weight: 0.080 g; yield percentage: 37%; solid; melting point: 81 to 82° C.; $^1$H-NMR (60 MHz, CDCl$_3$, δ): 6.8–7.7(5H, complex), 7.7–8.1(2H, complex), 8.60(1H, s), 10.29(1H, s)

EXAMPLE 11

Production of 4-methyl-6-[3-(trifluoromethyl) phenoxy] picolinic acid, (2,2,3,3,3-pentafluoropropylidene] hydrazide (compound No. I-51)

4-methyl-6-[3-(trifluoromethyl)phenoxy] picolinic acid hydrazide (0.38 g, 0.0012 mol) was dissolved in 5 ml of acetic acid. The obtained solution was mixed with 2,2,3,3,3-pentafluoropropionaldehyde monohydrate (0.40 g, 0.0012×2 mol), and then the resultant mixture was stirred at 80° C. for 3 hours. Thereafter, a chilled water was poured into the obtained reaction solution which was then distributed in ethyl acetate-water. The organic phase separated from the solution was washed with water and then dried with anhydrous sodium sulfate. After distilling off the solvent from the dried product, the obtained distillation residues were purified by silica gel column chromatography (eluting solution: ethyl acetate/hexane), thereby obtaining an aimed product.

Yield weight: 0.425 g; yield percentage: 79%; viscous substance; $^1$H-NMR (60 MHz, CDCl$_3$, δ): 2.40(3H, s), 6.9(1H, s), 7.0–7.5(5H, complex), 8.2(1H, t, J=6 Hz), 10.5 (1H, brs)

EXAMPLE 12

Production of 4-methoxy-6-[3-(trifluoromethyl) phenoxy] picolinic acid, (2-butynylidene] hydrazide (compound No. I-53)

2-butyne-1-al diethyl acetal (0.27 g, 0.000993×2 mol) was mixed with a 2N aqueous hydrochloric acid solution (about 3 ml) and 5 ml of benzene, and then the resultant mixture was stirred at about 70° C. for about 2 hours. After cooling to room temperature, the obtained mixture was mixed with 4-methoxy-6-[3-(trifluoromethyl)phenoxy] picolinic acid hydrazide (0.325 g, 0.000993 mol), and the resultant mixture was stirred at room temperature for 45 minutes. The obtained reaction solution was distributed in ethyl acetate-water, and the organic phase separated from the solution was washed with saturated brine, dried with anhydrous sodium sulfate and then concentrated. The obtained concentrated solution was purified by silica gel column chromatography (eluting solution: ethyl acetate/hexane), thereby obtaining an aimed product.

Yield weight: 0.24 g; yield percentage: 64%; solid; melting point: 147 to 148° C.; $^1$H-NMR (60 MHz, CDCl$_3$, δ): 1.65(3H, d, J=2 Hz), 3.88(3H, s), 6.55(1H, d, J=2 Hz), 6.6–6.8(1H, multi.), 7.2–7.5(4H, complex), 7.65(1H, d, J=2 Hz), 10.9–11.3(1H, br)

EXAMPLE 13

Production of 4-methoxy-6-[3-(trifluoromethyl) phenoxy] picolinic acid, (cyclopentylidene] hydrazide (compound No. I-100)

4-methoxy-6-[3-(trifluoromethyl)phenoxy] picolinic acid hydrazide (0.40 g, 0.0012 mol) was mixed cyclopentanone (1.0 g, 0.0012×10 mol) and then with diethyl ether (about 10 ml). The resultant mixture was stirred at room temperature for about one hour. The obtained reaction solution was concentrated, thereby obtaining an aimed product.

Yield weight: 0.48 g; yield percentage: 100%; solid; melting point: 146 to 148° C.; $^1$H-NMR (60 MHz, CDCl$_3$, δ): 1.3–2.0(6H, complex), 2.1–2.8(2H, complex), 3.86(3H, s), 6.52(1H, d, J=2 Hz), 6.9–7.7(5H, complex), 9.70(1H, s)

The properties and NMR data of the compounds obtained in the above Examples 1 to 13 and those produced according to the methods described therein, are shown in Tables 8 to 15 below.

In these Tables, the compounds (I-2), (I-14), (I-29) and (I-41) were measured at 250 MHz, and the other compounds were measured at 60 MHz.

TABLE 8

| Compound No. | Property | NMR CDCl$_3$, δ |
|---|---|---|
| I-2 | Solid m.p.154–155° C. | 1.00(1.8H,t,J = 7.3Hz), 1.10 (1.2H,t,J = 7.3Hz), 1.69(1.2H,dq,J = 5.4,7.3Hz). 2.38(0.8H,dq,J = 5.4,7.3Hz), 3.94(1.2H,s), 3.95(1.8H,s),6.55(0.4H,d, J = 2.4Hz),6.63(0.6H,d,J = 2.4 Hz), 6.77(0.6H,t,J = 5.4Hz), 7.0–7.7(5.4H,complex),10.00 (0.4H,s),10.21(0.6H,s). |
| I-5 | Solid m.p.147–148° C. | 3.89(3H,s),6.58(1H,d,J = 2Hz), 6.9–7.7(5H,complex),8.29 (1H,q,J = 4Hz), 10.47(1H,s). |
| I-6 | Solid m.p.107–108° C. | 3.87(3H,s),6.54(1H,d,J = 2Hz), 6.9–7.7(5H,complex),8.30 (1H,t,J = 6Hz), 10.52 (1H,s). |
| I-7 | Solid m.p.102 –103° C. | 3.86(3H,s),4.16(2H,d,J = 6Hz), 6.50(1H,d,J = 2Hz), 7.0–7.7 (6H,complex), 10.14(1H,s). |

TABLE 9

| Compound No. | Property | NMR CDCl$_3$, δ |
|---|---|---|
| I-14 | Solid m.p.125–127° C. | 0.2–1.0(4H,complex),1.19 (3H,s),1.7–2.0(1H,mult.),3.95 (3H,s),6.60(1H,d,J = 2.0Hz), 7.2–7.8(5H,complex), 9.99(1H,s). |
| I-15 | Solid m.p.98–100° C. | 3.39(2H,d,J = 4.5Hz),3.83(3H,s), 6.45(1H,d,J = 2Hz),6.9–7.6 (6H,complex), 10.24(1H,s). |
| I-16 | Solid m.p.134–136° C. | 1.43(3H,s),2.00(3H,s),3.86 (3H,s),6.55(1H,d,J = 2Hz), 7.0–7.8(5H,complex), 9.92(1H,s). |
| I-17 | Solid m.p.90–91° C. | 3.86(3H,s),6.52(1H,d,J = 2Hz), 6.5–7.6(4H,complex),7.46 (1H,d, = 2Hz),8.31(1H,t,J = 6Hz), 10.57(1H,s). |
| I-18 | Solid m.p.94–96° C. | 3.86(3H,s),6.53(1H,d,J = 2Hz), 6.9–7.6(5H,complex),8.24 (1H,t,J = 7Hz),10.49(1H,s). |

TABLE 10

| Compound No. | Property | NMR CDCl$_3$, δ |
|---|---|---|
| I-20 | Solid m.p.113–114° C. | 2.35(3H,s),3.82(3H,s),6.44 (1H,d,J = 2Hz),6.6–7.8(4H, complex),7.44(1H,d,J = 2Hz), 8.36(1H,t,J = 6Hz),10.73(1H,s). |
| I-22 | Solid m.p.116–117° C. | 3.83(3H,s),6.43(1H,d,J = 2Hz), 6.6–7.4(4H,complex),7.40(1H, d,J = 2Hz),8.33(1H,t,J = 7Hz), 10.58(1H,s). |
| I-27 | Solid m.p.112–113° C. | 1.47(3H,s),3.23(3H,s),3.88 (3H,s),3.99(2H,s),6.57(1H,d, J = 2Hz),7.2–7.7(5H,complex), 10.05(1H,s). |
| I-29 | Solid m.p.120–121° C. | 1.7–2.2(1.2H,complex),2.11 (2.1H,s).2.3–2.8(2.8H, complex),2.69(0.9H,s),3.93 (2.1H,s),3.95(0.9H,s),6.55 (0.7H,d,J = 2.0Hz),6.63(0.3H, d,J = 2.4Hz),6.89(0.3H,t, J = 5.1Hz),7.0–7.7(5.7H, complex),10.08(0.7H,s),10.23 (0.3H,s). |
| I-30 | Solid m.p.133–134° C. | 1.54(3H,s),3.89(3H,s),6.60 (1H,d,J = 2Hz),7.2–7.6(5H, complex),10.18(1H,s). |

TABLE 11

| Compound No. | Property | NMR CDCl$_3$, δ |
|---|---|---|
| I-31 | Solid m.p.84–86° C. | 3.88(3H,s),6.61(1H,d, J = 2Hz),6.9–7.6(5H,complex), 11.27(1H,s). |
| I-33 | Solid m.p.153–154° C. | 3.88(3H,s),6.52(1H,d,J = 2Hz), 6.5–7.1(2H,complex), 7.1–7.6(5H,complex), 7.8–8.3(2H,complex), 10.32(1H,s). |
| I-35 | Solid m.p.181–182° C. | 1.78(3H,s),3.87(3H,s),6.54 (1H,d,J = 2Hz),7.1–8.0(10H, complex),10.22(1H,s). |
| I-37 | Solid m.p.128–129° C. | 1.85(3H,d,J = 5Hz),3.85 (3H,s),5.8–6.4(2H,complex), 6.49(1H,d,J = 2Hz),7.1–7.6 (6H,complex),9.94(1H,s). |
| I-39 | Solid m.p.111–112° C. | 2.50(3H,s),6.82(1H,d, J = 2Hz),6.9–7.6(4H,complex), 7.68(1H,d,J = 2Hz),8.26(1H,t, J = 7Hz),10.44(1H,s). |
| I-40 | Solid m.p.108–109° C. | 3.02(6H,s),6.12(1H,d, J = 2Hz),6.9–7.6(5H,complex), 8.20(1H,t,J = 7Hz),10.65(1H,s). |

TABLE 12

| Compound No. | Property | NMR CDCl$_3$, δ |
|---|---|---|
| I-41 | Solid m.p.133–135° C. | 2.94(3H,d,J = 5.4Hz),4.5–4.9 (1H,m),6.17(1H,d,J = 2Hz), 7.0–7.7(5H,complex),8.24 (1H,dt,J = 1,6.8Hz),10.64(1H,s). |
| I-42 | Solid m.p.101–102° C. | 1.26(3H,t J = 7Hz),3.18(2H,dq, J = 5,7Hz),5.00(1H,t,J = 5Hz), 6.07(1H,d,J = 2Hz),6.8–7.6(5H, complex),7.99(1H,t,J = 7Hz), 10.67(1H,s). |
| I-45 | Solid m.p.83–85° C. | 1.21(3H,t,J = 7Hz),3.49(2H,q, J = 7Hz),4.51(2H,s),6.14(1H,d, J = 2Hz),6.8–7.7(10H,complex), 8.23(1H,t,J = 7Hz),10.69(1H,s). |
| I-47 | Solid m.p.130–131° C. | 7.05(1H,d,J = 8Hz),7.1–7.6(4H, complex),7.78(1H,d,J = 8Hz), 8.40(1H,t,J = 6Hz),10.0–10.3 (1H,br). |
| I-48 | Solid m.p.95–96° C. | 6.8–7.6(5H,complex),7.6–8.0 (2H,complex),8.27(1H,t,J = 7Hz), 10.47(1H,s). |

TABLE 13

| Compound No. | Property | NMR CDCl$_3$, δ |
|---|---|---|
| I-49 | Solid m.p.81–82° C. | 6.8–7.7(5H,complex),7.7–8.1 (2H,complex),8.60(1H,s), 10.29(1H,s). |

TABLE 13-continued

| Compound No. | Property | NMR CDCl$_3$, δ |
|---|---|---|
| I-50 | Solid m.p.113–114° C. | 3.88(3H,s),6.56(1H,d,J = 2Hz), 6.9–7.7(5H,complex),8.33 (1H,t,J = 5Hz),10.39(1H,s). |
| I-51 | Viscous material | 2.40(3H,s),6.9(1H,s),7.0–7.5 (4H,complex),8.2(1H,t,J = 6Hz), 10.5(1H,brs). |
| I-52 | Solid m.p.121–123° C. | 6.8–7.1(7H,complex,11.06(1H,s). |
| I-53 | Solid m.p.147–148° C. | 1.65(3H,d,J = 2Hz),3.88(3H,s), 6.55(1H,d,J = 2Hz),6.6–6.8 (1H,m),7.2–7.5(4H,complex), 7.65(1H,d,J = 2Hz), 10.9–11.3(1H,br). |
| I-54 | Solid m.p.86–88° C. | 3.87(3H,s),6.53(1H,d,J = 2Hz), 6.9–7.8(5H,complex),8.29 (1H,t,J = 7Hz),10.57(1H,s). |

TABLE 14

| Compound No. | Property | NMR CDCl$_3$, δ |
|---|---|---|
| I-100 | Solid m.p.146–148° C. | 1.3–2.0(6H,complex),2.1–2.8 (2H,complex),3.86(3H,s),6.52 (1H,d,J = 2Hz),6.9–7.7(5H, complex),9.70(1H,s). |
| I-101 | Solid m.p.149–151° C. | 1.3–2.0(6H,complex),2.0–2.7 (2H,complex),2.51(3H,s),6.86 (1H,d,J = 2Hz),7.0–7.7(4H, complex),7.75(1H,d,J = 2Hz), 9.64(1H,s). |
| I-102 | Solid m.p.154–155° C. | 1.4–2.0(6H,complex),2.1–2.8 (2H,complex),6.9–7.66(5H, complex),7.66–8.1(2H, complex),9.65(1H,s). |
| I-104 | Solid m.p.146–147° C. | 1.87(2H,t,J = 6Hz),2.50(2H,t, J = 6chz),3.3–4.1(4H,complex), 3.89(3H,s)6.57(1H,d,J = 2Hz), /7.1–&.7(5H,complex),10.13 (1H,s). |
| I-105 | Solid m.p.135–136° C. | 1.8–2.3(2H,complex),2.3–3.0 (6H,complex),3.87(3H,s),6.54 (1H,d,J = 2Hz), 7.0–7.7(5H, complex),10.08(1H,s). |

TABLE 15

| Compound No. | Property | NMR CDCl$_3$, δ |
|---|---|---|
| I-106 | Solid m.p.175–176° C. | 1.87(2H,t,J = 6Hz),2.0–2.7 (6H,complex),2.51(3H,s), 3.90(3H,s)6.58(1H,d,J = 2Hz), 7.0–7.7(5H,complex).10.09 (1H,s). |

The compounds (II) used above were produced by the following methods.

REFERENCE PRODUCTION EXAMPLE 1

Production of 4-methoxy-6-[3-(trifluoromethyl) phenoxy] picolinic acid hydrazide (compound No. II-1)

(1) <Production of 4-methoxy-6-[3-(trifluoromethyl) phenoxy] picolinic acid, N',N'-dibenzyl hydrazide (compound No. V-1) as an intermediate product>

4-methoxy-6-[3-(trifluoromethyl)phenoxy] picolinic acid (5.0 g, 0.016 mol) was mixed with thionyl chloride (3.75 g, 0.016×2.0 mol) and benzene (about 50 ml), and further with a small amount of dimethyl formamide. Thereafter, the resultant mixture was refluxed for about one hour. The obtained reaction solution was concentrated and then dissolved in dichloromethane (about 150 ml). The obtained solution was mixed with N,N-dibenzyl hydrazide (5.13 g, 0.016×1.5 mol) and further with triethyl amine (3.9 g, 0.016×2.4 mol), and the resultant mixture was stirred at room temperature for about one hour. Thereafter, the obtained reaction solution was distributed in ethyl acetate-saturated sodium bicarbonate water, and the organic phase separated from the solution was washed with saturated brine, dried with anhydrous sodium sulfate and then concentrated. The obtained concentrated solution was purified by silica gel column chromatography (eluting solution: ethyl acetate/hexane), thereby obtaining an aimed product.

Yield weight: 7.38 g; yield percentage: 91%; solid; melting point: 91 to 94° C.; $^1$H-NMR (60 MHz, CDCl$_3$, δ): 3.73(3H, s), 3.92(4H, s), 6.35(1H, d, J=2 Hz), 6.7–7.6(15H, complex), 8.00(1H, s)

(2) <Production of 4-methoxy-6-[3-(trifluoromethyl) phenoxy] picolinic acid hydrazide (compound No. II-1)>

4-methoxy-6-[3-(trifluoromethyl)phenoxy] picolinic acid, N',N'-dibenzyl hydrazide (7.38 g, 0.0145 mol) was mixed with a mixed solution of ethyl acetate (about 50 ml) and methanol (about 50 ml), and further with 10% palladium/carbon (1.0 g, 0.0145×0.065 mol) in a hydrogen atmosphere. The resultant mixture was stirred at a temperature of 50 to 60° C. for about 5 hours. The obtained reaction solution was filtered and concentrated, thereby obtaining an aimed product.

Yield weight: 4.10 g; yield percentage: 86%; solid; melting point: 147 to 148° C.; $^1$H-NMR (250 MHz, CDCl$_3$, δ): 3.5–4.2(2H, br), 3.93(3H, s), 6.49(1H, d, J=2.0 Hz), 7.0–7.7 (5H, complex), 8.32(1H, s)

REFERENCE PRODUCTION EXAMPLE 2

Production of 4-methylmercapto-6-[3-(trifluoromethyl) phenoxy] picolinic acid hydrazide (compound No. II-2)

4-methylmercapto-6-[3-(trifluoromethyl)phenoxy] picolinic acid (0.65 g, 0.0020 mol) was mixed with thionyl chloride (0.47 g, 0.0020×2.0 mol) and benzene (about 10 ml), and further with a small amount of dimethyl formamide. Thereafter, the resultant mixture was refluxed for about one hour. The obtained reaction solution was concentrated and then dissolved in 1,4-dioxane (about 10 ml). The obtained solution was mixed with a solution obtained by adding 4-dioxane (about 10 ml) to hydrazide monohydrate (2.0 g, 0.0020×20 mol), and the resultant mixture was stirred at room temperature for about one hour. Thereafter, the obtained reaction solution was distributed in ethyl acetate-saturated sodium bicarbonate water, and the organic phase separated from the solution was washed with saturated brine, dried with anhydrous sodium sulfate and then concentrated. The obtained concentrated solution was mixed with diethyl ether and then filtered to remove insoluble components therefrom. After the filtrate was concentrated, the obtained residues were purified by silica gel column chromatography (eluting solution: ethyl acetate/hexane), thereby obtaining an aimed product.

Yield weight: 0.17 g; yield percentage: 25%; solid; melting point: 149 to 151° C.; $^1$H-NMR (60 MHz, CDCl$_3$, δ): 2.49(3H, s), 3.87(2H, br), 6.79(1H, d, J=2 Hz), 7.0–7.6(4H, complex), 7.63(1H, d, J=2 Hz), 8.31(1H, br)

REFERENCE PRODUCTION EXAMPLE 3

Production of 4-dimethylamino-6-[3-(trifluoromethyl)phenoxy] picolinic acid hydrazide (compound No. II-3)

(1) <Production of 4-dimethylamino-6-[3-(trifluoromethyl)phenoxy] picolinic acid, N',N'-dibenzyl hydrazide (compound No. V-3) as an intermediate product>

4-dimethylamino-6-[3-(trifluoromethyl)phenoxy] picolinic acid (0.64 g, 0.0020 mol) was mixed with thionyl chloride (0.50 g, 0.0020×2.1 mol) and benzene (about 10 ml), and further with a small amount of dimethyl formamide. Thereafter, the resultant mixture was refluxed for about 30 minutes. The obtained reaction solution was concentrated and then dissolved in dichloromethane (about 30 ml). The obtained solution was mixed with N,N-dibenzyl hydrazine (0.66 g, 0.0020×1.6 mol) and further with triethyl amine (0.53 g, 0.0020×2.6 mol). After the resultant mixture was stirred at room temperature for about one hour, the obtained reaction solution was distributed in ethyl acetate-saturated sodium bicarbonate water, and the organic phase separated from the solution was washed with saturated brine, dried with anhydrous sodium sulfate and then concentrated. The obtained concentrated solution was purified by silica gel column chromatography (eluting solution: ethyl acetate/hexane), thereby obtaining an aimed product.

Yield weight: 0.92 g; yield percentage: 90%; solid; melting point: 68 to 70° C.; $^1$H-NMR (60 MHz, CDCl$_3$, δ): 2.90(6H, s), 3.93(4H, s), 5.78(1H, d, J=2 Hz), 6.8–7.6(15H, complex), 8.16(1H, s)

(2) <Production of 4-dimethylamino-6-[3-(trifluoromethyl)phenoxy] picolinic acid hydrazide (compound No. II-3)>

4-dimethylamino-6-[3-(trifluoromethyl)phenoxy] picolinic acid, N',N'-dibenzyl hydrazide (0.80 g, 0.00154 mol) was mixed with methanol (about 10 ml), and further with 10% palladium/carbon (0.2 g, 0.00154×0.12 mol) in a hydrogen atmosphere (about 0.5 kg/cm$^2$). The resultant mixture was stirred at a temperature of about 50 to 60° C. for about 3 hours. The obtained reaction solution was filtered and concentrated, thereby obtaining an aimed product.

Yield weight: 0.51 g; yield percentage: 98%; solid; melting point: 58 to 62° C.; $^1$H-NMR (250 MHz, CDCl$_3$, δ): 3.01(6H, s), 5.0–8.0(3H, br), 5.80(1H, brs), 6.9–8.8(5H, complex)

REFERENCE PRODUCTION EXAMPLE 4

Production of 4-ethylamino-6-[3-(trifluoromethyl)phenoxy] picolinic acid hydrazide (compound No. II-6)

(1) <Production of 4-ethyl(phenylmethyl)amino-6-[3-(trifluoromethyl)phenoxy] picolinic acid, N',N'-dibenzyl hydrazide (compound No. V-4) as an intermediate product>

4-ethyl(phenylmethyl)amino-6-[3-(trifluoromethyl)phenoxy] picolinic acid (0.80 g, 0.0019 mol) was mixed with thionyl chloride (0.46 g, 0.0019×2.0 mol) and benzene (about 15 ml), and further with a small amount of dimethyl formamide. Thereafter, the resultant mixture was refluxed for about one hour. The obtained reaction solution was concentrated and then dissolved in dichloromethane (about 30 ml). The obtained solution was mixed with N,N-dibenzyl hydrazine (0.61 g, 0.0019×1.5 mol) and further with triethyl amine (0.49 g, 0.0019×2.5 mol), and the resultant mixture was stirred at room temperature for about one hour. Thereafter, the obtained reaction solution was distributed in ethyl acetate-saturated sodium bicarbonate water, and the organic phase separated from the solution was washed with saturated brine, dried with anhydrous sodium sulfate and then concentrated. The obtained concentrated solution was treated with a silica gel column, thereby obtaining a mixture containing N,N-dibenzyl hydrazine as the raw material and the compound (V-4). The thus obtained mixture was dissolved again in dichloromethane, and mixed with methanesulfonyl chloride (0.44 g, 0.0019×2.0 mol) and triethyl amine (0.49 g, 0.0019×2.5 mol). After the resultant mixture was stirred at room temperature for about one hour, the obtained reaction solution was distributed in ethyl acetate-saturated sodium bicarbonate water, and the organic phase separated from the solution was washed with saturated brine, dried with anhydrous sodium sulfate and then concentrated. The obtained concentrated solution was purified by silica gel column chromatography (eluting solution: ethyl acetate/hexane), thereby obtaining 4-ethyl(phenylmethyl)amino-6-[3-(trifluoromethyl)phenoxy] picolinic acid N',N'-dibenzyl hydrazide (compound No. V-4).

Yield weight: 0.98 g; yield percentage: 84%; solid; melting point: 104 to 109° C.; $^1$H-NMR (60 MHz, CDCl$_3$, δ): 1.13(3H, t, J=7 Hz), 3.39(2H, q, J=7 Hz), 3.94(4H, s), 4.41(2H, s), 6.00(1H, d, J=2 Hz), 6.8–7.6(20H, complex), 8.20(1H, s)

(2) <Production of 4-ethylamino-6-[3-(trifluoromethyl)phenoxy] picolinic acid hydrazide (compound No. II-6)>

4-ethyl(phenylmethyl)amino-6-[3-(trifluoromethyl)phenoxy] picolinic acid, N',N'-dibenzyl hydrazide (0.90 g, 0.00148 mol) was mixed with methanol (about 10 ml), and further with 10% palladium/carbon (0.5 g, 0.00147×0.32 mol) in a hydrogen atmosphere (about 0.5 kg/cm$^2$). The resultant mixture was stirred at a temperature of about 50 to 60° C. for about 5 hours. The obtained reaction solution was filtered and concentrated, thereby obtaining 4-ethylamino-6-[3-(trifluoromethyl)phenoxy] picolinic acid hydrazide.

Yield weight: 0.48 g; yield percentage: 96%; solid; melting point: 103 to 109° C.; $^1$H-NMR (250 MHz, CDCl$_3$, δ): 0.5–1.5(3H, br), 2.3–3.3(2H, br), 4.9–5.8(1H, br), 6.5–7.8 (5H, complex), 7.5–10.5(3H, br), 1H of ethylamino was unclear.

REFERENCE PRODUCTION EXAMPLE 5

Production of 4-methoxy-6-[3-(trifluoromethoxy)phenoxy] picolinic acid hydrazide (compound No. II-7)

(1) <Production of 4-methoxy-6-[3-(trifluoromethoxy)phenoxy] picolinic acid methyl ester (compound No. IV-b-2) as an intermediate product>

4-methoxy-6-[3-(trifluoromethoxy)phenoxy] picolinic acid (0.8 g, 0.0024 mol) was mixed with thionyl chloride (0.58 g, 0.0024×2.0 mol) and benzene (about 10 ml), and further with a small amount of dimethyl formamide. Thereafter, the resultant mixture was refluxed for about one hour. The obtained reaction solution was concentrated and then dissolved in dichloromethane. The obtained solution was added to a methanol solution (about 10 ml) containing triethyl amine (0.52 g, 0.0024×2 mol), and the resultant mixture was stirred at room temperature for about one hour. Thereafter, the obtained reaction solution was concentrated and dissolved in ethyl acetate, and then distributed in ethyl acetate-saturated sodium bicarbonate water. The organic phase separated from the solution was washed with saturated brine, dried with anhydrous sodium sulfate and then concentrated. The obtained concentrated solution was purified by silica gel column chromatography (eluting solution: ethyl acetate/hexane), thereby obtaining an aimed product.

Yield weight: 0.84 g; yield percentage: 100%; solid; melting point: 63 to 64° C.; $^1$H-NMR (60 MHz, CDCl$_3$, δ): 3.77(3H, s), 3.81(3H, s), 6.38(1H, d, J=2 Hz), 6.7–7.6(4H, complex), 7.33(1H, d, J=2 Hz)

(2) <Production of 4-methoxy-6-[3-(trifluoromethoxy) phenoxy] picolinic acid hydrazide (compound No. II-7)>

4-methoxy-6-[3-(trifluoromethoxy)phenoxy] picolinic acid methyl ester (0.74 g, 0.00216 mol) was dissolved in methanol (about 10 ml), and then mixed with hydrazine monohydrate (1.08 g, 0.00216×10 mol). The resultant mixture was refluxed for about 3 hours. The obtained reaction solution was concentrated and dissolved in ethyl acetate, and then distributed in ethyl acetate-saturated sodium bicarbonate water. The organic phase separated from the solution was washed with saturated brine, dried with anhydrous sodium sulfate and then concentrated, thereby obtaining an aimed product.

Yield weight: 0.63 g; yield percentage: 85%; solid; melting point: 128 to 130° C.; $^1$H-NMR (60 MHz, CDCl$_3$, δ): 3.83(3H, s), 3.92(2H, brs), 6.45(1H, d, J=2 Hz), 6.7–7.6(4H, complex), 7.42(1H, d, J=2 Hz), 8.40(1H, brs)

REFERENCE PRODUCTION EXAMPLE 6

Production of 4-methoxy-6-(3-chlorophenoxy) picolinic acid hydrazide (compound No. II-10)

(1) <Production of 4-methoxy-6-(3-chlorophenoxy) picolinic acid methyl ester (compound No. IV-b-5) as an intermediate product>

4-methoxy-6-(3-chlorophenoxy) picolinic acid (1.0 g, 0.00358 mol) was mixed with thionyl chloride (0.85 g, 0.00358×2.0 mol) and benzene (about 10 ml), and further with a small amount of dimethyl formamide. The resultant mixture was refluxed for about one hour. The obtained reaction solution was concentrated and then dissolved in dichloromethane. The obtained solution was added to a methanol solution (about 10 ml) containing triethyl amine (0.54 g, 0.0358×1.5 mol), and then stirred at room temperature for about one hour. Thereafter, the obtained reaction solution was concentrated and dissolved in ethyl acetate, and then distributed in ethyl acetate-saturated sodium bicarbonate water. The organic phase separated from the solution was washed with saturated brine, dried with anhydrous sodium sulfate and then concentrated. The obtained concentrated solution was purified by silica gel column chromatography (eluting solution: ethyl acetette/hexane), thereby obtaining an aimed product.

Yield weight: 0.88 g; yield percentage: 84%; solid; melting point: 100 to 102° C.; $^1$H-NMR (60 MHz, CDCl$_3$, δ): 3.77(3H, s), 3.83(3H, s), 6.45(1H, d, J=2 Hz), 6.7–7.4(4H, complex), 7.33(1H, d, J=2 Hz)

(2)-Production of 4-methoxy-6-(3-chlorophenoxy) picolinic acid hydrazide (compound No. II-10)>

4-methoxy-6-(3-chlorophenoxy) picolinic acid methyl ester (0.77 g, 0.00262 mol) was dissolved in methanol (about 10 ml), and then mixed with hydrazine monohydrate (1.31 g, 0.00262×10 mol). The resultant reaction was refluxed for about 1.5 hours. The obtained reaction solution was concentrated and dissolved in ethyl acetate, and then distributed in ethyl acetate-saturated sodium bicarbonate water. The organic phase separated from the solution was washed with saturated brine, dried with anhydrous sodium sulfate and then concentrated, thereby obtaining an aimed product.

Yield weight: 0.77 g; yield percentage: 100%; solid; melting point: 135 to 136° C.; $^1$H-NMR (60 MHz, CDCl$_3$, δ): 3.83(5H, s), 6.42(1H, d, J=2 Hz), 6.7–7.5(4H, complex), 7.41(1H, d, J=2 Hz), 8.44(1H, brs)

REFERENCE PRODUCTION EXAMPLE 7

Production of 3-chloro-6-[3-(trifluoromethyl) phenoxy]-picolinic acid hydrazide (compound No. II-11)

(1) <Production of 3-chloro-6-[3-(trifluoromethyl) phenoxy]-picolinic acid methyl ester (compound No. IV-b-6)>

3-chloro-6-[3-(trifluoromethyl)phenoxy]-2-picolinic acid (1.53 g, 0.0048 mol) was suspended in 20 ml of benzene containing a catalytic amount of dimethyl formamide (DMF). The obtained suspension was mixed with thionyl chloride (2.86 g, 0.0048×5 mol), and the resultant mixture was refluxed for one hour. Thereafter, the obtained solution was distilled to completely remove benzene and an excess amount of thionyl chloride therefrom. The resultant distillation residues were added to dried methanol (about 30 ml) containing triethyl amine (0.53 g, 0.0048×1.1 mol), and stirred at room temperature for 1.5 hours. The obtained reaction solution was subjected to distillation, and the distillation residues were distributed in ethyl acetate-water. The organic phase separated from the solution was washed with water and then dried with anhydrous sodium sulfate. After distilling off the solvent, the obtained concentrated solution was purified by silica gel column chromatography (eluting solution: ethyl acetate/hexane), thereby obtaining an aimed product.

Yield weight: 0.73 g; yield percentage: 46%; viscous substance; $^1$H-NMR (60 MHz, CDCl$_3$, δ) 3.78(3H, s), 6.88(1H, d, J=8 Hz), 7.1–7.5(4H, complex), 7.67(1H, d, J=8 Hz)

(2) <Production of 3-chloro-6-[3-(trifluoromethyl)phenoxy] picolinic acid hydrazide (compound No. II-11)>

3-chloro-6-[3-(trifluoromethyl)phenoxy]-2-picolinic acid methyl ester (0.72 g, 0.00217 mol) was dissolved in methanol (10 ml), and then mixed with hydrazine monohydrate (1.087 g, 0.00217×10 mol). The resultant mixture was refluxed for about 3 hours. The obtained reaction solution was concentrated, and the obtained residues were distributed in ethyl acetate-saturated sodium bicarbonate water. The organic phase separated from the solution was washed with water and then dried with anhydrous sodium sulfate. After distilling off the solvent, the obtained distillation residues were purified by silica gel column chromatography (eluting solution: ethyl acetate/hexane), thereby obtaining an aimed product.

Yield weight: 0.67 g; yield percentage: 93%; solid; melting point: 102 to 104° C.; $^1$H-NMR (60 MHz, CDCl$_3$, δ): 3.6–4.1(2H, br), 6.93(1H, d, J=8 Hz), 7.1–7.6(4H, complex), 7.68(1H, d, J=8 Hz), 8.0–8.4(1H, br)

REFERENCE PRODUCTION EXAMPLE 8

Production of 4-methyl-6-[3-(trifluoromethyl)-phenoxy] picolinic acid hydrazide (compound No. II-12)

(1) <Production of 4-methyl-6-[3-(trifluoromethyl) phenoxy]-picolinic acid methyl ester (compound No. IV-b-7)>

4-methyl-6-[3-(trifluoromethyl)phenoxy] picolinic acid (0.525 g, 0.00177 mol) was suspended in 6 ml of benzene containing a catalytic amount of dimethyl formamide (DMF), and the obtained suspension was mixed with thionyl chloride (1.05 g, 0.000177×5 mol). The resultant mixture was refluxed for one hour. Thereafter, the obtained solution was distilled to completely remove benzene and an excess amount of thionyl chloride therefrom. The obtained residues were added to 10 ml of methanol containing triethyl amine (0.196 g, 0.00177×1.1 mol), and the resultant mixture was stirred at room temperature for 1.5 hours. The obtained reaction solution was distilled, and the resultant distillation residues were distributed in ethyl acetate-water. The organic phase separated from the solution was washed with water and then dried with anhydrous sodium sulfate. After distilling off the solvent, the obtained concentrated solution was purified by silica gel column chromatography (eluting solution: ethyl acetate/hexane), thereby obtaining an aimed product.

Yield weight: 0.507 g; yield percentage: 92%; solid; $^1$H-NMR (60 MHz, CDCl$_3$, δ): 2.35(3H, s), 3.8(3H, s), 6.78(1H, s), 7.1–7.5(4H, complex), 7.62(1H, s)

(2) <Production of 4-methyl-6-[3-(trifluoromethyl)phenoxy] picolinic acid hydrazide (compound No. II-12)>

4-methyl-6-[3-(trifluoromethyl)phenoxy] picolinic acid methyl ester (0.507 g, 0.00163 mol) was dissolved in 10 ml of methanol, and then mixed with hydrazine monohydrate (0.816 g, 0.00163×10 mol). The resultant mixture was refluxed for about 3 hours. The obtained reaction solution was concentrated, and the obtained residues were distributed in ethyl acetate-saturated sodium bicarbonate water. The organic phase separated from the solution was washed with water and then dried with anhydrous sodium sulfate. After distilling off the solvent, the obtained residues were purified by silica gel column chromatography (eluting solution: ethyl acetate/hexane), thereby obtaining an aimed product.

Yield weight: 0.38 g; yield percentage: 75%; solid; melting point: 143 to 144° C.; $^1$H-NMR (60 MHz, CDCl$_3$, δ): 2.40(3H, s), 3.6–3.9(2H, br), 6.83(1H, s), 7.0–7.5(4H, complex), 7.66(1H, s), 8.0–8.4(1H, br)

The compounds obtained in the above Reference Production Examples 1 to 8 as well as compounds produced according to the methods described therein are shown in Tables 16, 20 and 22, and the properties and NMR data of these compounds are shown in Tables 17 to 19, 21 and 22.

In Table 12, the compounds (II-1), (II-3), (II-4), (II-5), (II-6) and (II-13) were measured at 250 MHz, and the other compounds were measured at 60 MHz.

TABLE 16

| Compound No. | Substituent R$^1$ | Y |
|---|---|---|
| II-1 | 4-OCH$_3$ | 3-CF$_3$ |
| II-2 | 4-SCH$_3$ | 3-CF$_3$ |
| II-3 | 4-N(CH$_3$)$_2$ | 3-CF$_3$ |
| II-4 | 4-NCH$_2$CH$_3$(CH$_2$Ph) | 3-CF$_3$ |
| II-5 | — | 3-CF$_3$ |
| II-6 | 4-NHCH$_2$CH$_3$ | 3-CF$_3$ |
| II-7 | 4-OCH$_3$ | 3-OCF$_3$ |
| II-8 | 4-OCH$_3$ | 3-SCF$_3$ |
| II-9 | 4-OCH$_3$ | 3-CH$_3$ |
| II-10 | 4-OCH$_3$ | 3-Cl |
| II-11 | 3-Cl | 3-CF$_3$ |
| II-12 | 4-CH$_3$ | 3-CF$_3$ |
| II-13 | 4-NHCH$_3$ | 3-CF$_3$ |

TABLE 17

| Compound No. | Property | NMR CDCl$_3$, δ |
|---|---|---|
| II-1 | Solid m.p.147–148° C. | 3.5–4.2(2H,br),3.93(3H,s), 6.49(1H,d,J = 2.0Hz), 7.0–7.7(5H,complex), 8.32(1H,s). |

TABLE 17-continued

| Compound No. | Property | NMR CDCl$_3$, δ |
|---|---|---|
| II-2 | Solid m.p.149–151° C. | 2.49(3H,s),3.87(2H,br), 6.79(1H,d,J = 2Hz),7.0–7.6 (4H,complex),7.63(1H,d, J = 2Hz),8.31(1H,br). |
| II-3 | Solid m.p.58–62° C. | 3.01(6H,s),5.0–8.0(3H,br), 5.80(1H,brs),6.9–8.8(5H, complex). |
| II-4 | Solid m.p.100–104° C. | 1.25(3H,t,J = 7.0Hz),3.55 (2H,q,J = 7.0Hz),2.5–4.5 (2H,br),4.60(2H,s),6.16 (1H,d,J = 2.4Hz),6.9–7.5 (10H,complex),8.40(1H,s). |
| II-5 | Viscous material | 4.0–6.8(3H,br),6.7–8.0 (7H,complex) |

TABLE 18

| Compound No. | Property | NMR CDCl$_3$, δ |
|---|---|---|
| II-6 | Solid m.p.103–109° C. | 0.5–1.5(3H,br),2.3–3.3(2H,br), 4.9–5.8(1H,br),6.5–7.8(5H, complex),7.5–10.5(3H,br),1H of ethylamino group: unclear |
| II-7 | Solid m.p.128–130° C. | 3.83(3H,s),3.92(2H,brs), 6.45(1H,d,J = 2Hz),6.5–7.6 (4H,complex),7.42(1H,d, J = 2Hz),8.40(1H,s). |
| II-8 | Solid m.p.142–143° C. | 3.85(5H,s),6.46(1H,d,J = 2Hz), 6.6–7.7(5H,complex), 8.40(1H,s). |
| II-9 | Solid m.p.114–115° C. | 2.30(3H,s),3.77(3H,s),3.88 (2H,brs),6.33(1H,d,J = 2Hz), 6.6–7.3(4H,complex),7.33 (1H,d,J = 2Hz),8.72(1H,s). |
| II-10 | Solid m.p.135–136° C. | 3.83(5H,s),6.42(1H,d,J = 2Hz), 6.7–7.5(4H,complex). 7.41(1H,d,J = 2Hz),8.44(1H,s). |

TABLE 19

| Compound No. | Property | NMR CDCl$_3$, δ |
|---|---|---|
| II-11 | Solid m.p.102–104° C. | 3.6–4.1(2H,br),6.93(1H,d, J = 8Hz),7.1–7.6(4H,complex), 7.68(1H,d,J = 8Hz),8.0–8.4 (1H,br). |
| II-12 | Solid m.p.102–104° C. | 2.40(3H,s),3.6–3.9(2H,br), 6.83(1H,s),7.0–7.5(4H, complex),7.66(1H,s),8.0–8.4 (1H,br). |
| II-13 | Viscous material | 1.8–3.0(3H,br),4.8–5.8(1H,br), 6.2–7.8(5H,complex),7.2–10.0 (3H,br),1H of methylamino group: unclear |

TABLE 20

| Compound No. | Substituent R$^{1a}$ | Y |
|---|---|---|
| IV-b-1 | 4-OCH$_3$ | 3-CF$_3$ |
| IV-b-2 | 4-OCH$_3$ | 3-OCF$_3$ |
| IV-b-3 | 4-OCH$_3$ | 3-SCF$_3$ |
| IV-b-4 | 4-OCH$_3$ | 3-CH$_3$ |
| IV-b-5 | 4-OCH$_3$ | 3-Cl |
| IV-b-6 | 4-Cl | 3-CF$_3$ |

TABLE 20-continued

| Compound | Substituent | |
|---|---|---|
| No. | R$^{1a}$ | Y |
| IV-b-7 | 4-CH$_3$ | 3-CF$_3$ |
| IV-b-8 | — | 3-CF$_3$ |

TABLE 21

| Compound No. | Property | NMR 60MHz,CDCl$_3$, δ |
|---|---|---|
| IV-b-1 | Solid m.p.78–79° C. | 3.81(6H,s),6.40(1H,d,J = 2Hz), 7.1–7.5(5H,complex). |
| IV-b-2 | Solid m.p.63–64° C. | 3.77(3H,s),3.81(3H,s),6.38 (1H,d,J = 2Hz),6.7–7.6(4H, complex),6.33(1H,d,J = 2Hz). |
| IV-b-3 | Solid m.p.76–77° C. | 3.78(3H,s),3.81(3H,s),6.40 (1H,d,J = 2Hz),7.1–7.6(5H, complex |
| IV-b-4 | Oily material | 2.29(3H,s),3.74(3H,s),3.83 (3H,s),6.26(1H,d,J = 2Hz), 6.6–7.4(4H,complex),7.31 (1H,d,J = 2Hz), |
| IV-b-5 | Solid m.p.100–102° C. | 3.77(3H,s),3.83(3H,s),6.45 (1H,d,J = 2Hz),6.7–7.4(4H, complex),7.33(1H,d,J = 2Hz). |
| IV-b-6 | Viscous material | 3.78(3H,s),6.88(1H,d,J = 8Hz), 7.1–7.5(4H,complex),7.67 (1H,d,J = 8Hz). |
| IV-b-7 | Solid | 2.35(3H,s),3.8(3H,s),6.78 (1H,s),7.1–7.5(4H,complex), 7.62(1H,s). |
| IV-b-8 | Oily material | 3.81(3H,s),6.8–8.1(4H, complex). |

TABLE 22

| Compound | Substituent | |
|---|---|---|
| No. | R$^{1a}$ | Y |
| V-1 | 4-OCH$_3$ | 3-CF$_3$ |
| V-2 | 4-SCH$_3$ | 3-CF$_3$ |
| V-3 | 4-N(CH$_3$)$_2$ | 3-CF$_3$ |
| V-4 | 4-NCH$_2$CH$_3$(CH$_2$Ph) | 3-CF$_3$ |
| V-5 | — | 3-CF$_3$ |
| V-6 | 4-NCH$_3$(CH$_2$Ph) | 3-CF$_3$ |

TABLE 23

| Compound No. | Property | NMR 60MHz,CDCl$_3$,δ |
|---|---|---|
| V-1 | Solid m.p.91–94° C. | 3.73(3H,s),3.92(4H,s),6.35 (1H,d,J = 2Hz),6.7–7.6(15H, complex),8.00(1H,s). |
| V-2 | Oily material | 2.42(3H,s),3.94(4H,s),6.71 (1H,d,J = 2Hz),6.8–7.6(14H, complex),6.71(1H,d,J = 2Hz), 8.00(1H,s). |
| V-3 | Solid m.p.68–70° C. | 2.90(6H,s),3.93(4H,s),5.98 (1H,d,J = 2Hz),6.8–7.6(15H, complex),8.16(1H,s). |
| V-4 | Solid m.p.59–61° C. | 1.13(3H,t,J = 7Hz),3.39(2H, q,J = 7Hz),3.94(4H,s),4.41 (2H,s),6.00(1H,d,J = 2Hz), 6.8–7.6(20H,complex), 8.20(1H,s). |

TABLE 23-continued

| Compound No. | Property | NMR 60MHz,CDCl$_3$,δ |
|---|---|---|
| V-5 | Oily material | 3.95(4H,s),6.7–7.6(15H, complex),7.6–7.9(2H, complex),7.99(1H,s). |
| V-6 | Oily material | 3.02(3H,s),3.94(4H,s),4.51 (2H,s),6.06(1H,d,J-2Hz), 6.8–7.7(20H,complex),8.19 (1H,s). |

The compounds (VI) used above were produced by the following methods.

REFERENCE PRODUCTION EXAMPLE 9

Production of 4-methoxy-6-[3-(trifluoromethyl) phenoxy] picolinic acid (compound No. VI-1)

(1) <Production of 2-bromo-4-methoxy-6-[3-(trifluoromethyl)phenoxy] pyridine as an intermediate product>

3-(trifluoromethyl) phenol (3.34 g; 0.0187×1.1 mol) was dissolved in dimethyl formamide (about 30 ml). Further, sodium hydride [0.78 g (ca. 60% in mineral oil), 0.0187×1.0 mol] and then 2,6-dibromo-4-methoxy pyridine (5.00 g, 0.0187 mol) were added to the solution. The obtained solution was stirred at about 120° C. for about 2 hours and, thereafter, allowed so as to stand and cooled to room temperature. The obtained reaction solution was distributed in hexane-saturated sodium bicarbonate water. The organic phase separated from the reaction solution was washed with saturated brine, and dried with anhydrous sodium sulfate. The resultant solution was concentrated and then purified by silica gel column chromatography (eluting solution: ethyl acetate/hexane), and the obtained purified product was subjected to recrystallization using hexane, thereby obtaining an aimed product.

Yield weight: 3.23 g; yield percentage: 50%; solid; melting point: 57 to 60° C.; $^1$H-NMR (60 MHz, CDCl$_3$, δ): 3.75(3H, s), 6.26(1H, d, J=2 Hz), 6.75(1H, d, J=2 Hz), 7.0–7.6(4H, complex).

(2) <Production of 4-methoxy-6-[3-(trifluoromethyl) phenoxy] picolinic acid (compound No. VI-1)>

2-bromo-4-methoxy-6-[3-(trifluoromethyl)phenoxy] pyridine (3.00 g, 0.0086 mol) was suspended in about 30 ml of diethyl ether. While cooling in a dry ice-acetone bath in an argon atmosphere, the obtained suspension was mixed with n-butyl lithium [5.9 ml (ca. 1.69M hexane solution), 0.0086×1.1 mol], and the obtained suspension was stirred for about 10 minutes. After replacing an interior of the reactor with a carbon dioxide gas, the solution was removed from the bath and stirred at room temperature for about one hour. The obtained reaction solution was mixed with about 10 ml of a 1N aqueous hydrochloric acid solution, distributed in ethyl acetate-water, and then washed with saturated brine. The organic phase separated from the solution was dried with anhydrous sodium sulfate, concentrated and purified by silica gel column chromatography (eluting solution: ethyl acetate/hexane), thereby obtaining an aimed product.

Yield weight: 0.82 g; yield percentage: 30%; solid; melting point: 85 to 88° C.; $^1$H-NMR (60 MHz, CDCl$_3$, δ): 3.84(3H, s), 6.55(1H, d, J=2 Hz), 7.0–7.6(5H, complex), 9.61(1H, s).

REFERENCE PRODUCTION EXAMPLE 10

Production of 4-methoxy-6-[3-(trifluoromethyl) phenoxy] picolinic acid (compound No. VI-1)

(1) <Production of 2-chloro-4-nitro pyridine N-oxide as an intermediate product>

2-chloro pyridine N-oxide hydrochloride (17.0 g, 0.102 mol) was mixed with sulfuric acid (64.0 g, 0.102×6.4 mol) and fuming nitric acid (36.0 g (ca. 94%), 0.102×5.3 mol), and the obtained mixture was stirred at a temperature of 90 to 100° C. for 2.5 hours. The obtained reaction mixture was added to 800 ml of ice water to form a precipitate. The precipitate was filtered out, washed with water and then dried. The water phase was extracted with ethyl acetate. The obtained extract was recrystallized with ethyl acetate and hexane.

Yield weight: 14.4 g; yield percentage: 81%; solid; melting point: 151 to 153° C.; $^1$H-NMR (60 MHz, CDCl$_3$, δ): 7.7–8.2(1H, multi.), 8.2–8.6(2H, complex).

(2) <Production of 2-chloro-4-methoxy pyridine N-oxide as an intermediate product>

2-chloro-4-nitro pyridine N-oxide (13.4 g, 0.077 mol) was suspended in 100 ml of methanol. Sodium methoxide [14.8 g (ca. 28% methanol solution), 0.077×1.0 mol] was dropped into the obtained suspension and dissolved therein at room temperature while stirring, and the suspension was further stirred for 2 days. The obtained reaction solution was distilled under reduced pressure to remove methanol therefrom. The distillation residue was dissolved in ethyl acetate. The obtained solution was filtered to remove sodium nitrite therefrom, and then ethyl acetate was distilled off, thereby obtaining an aimed product.

Yield weight: 12.1 g; yield percentage: 99%; solid; decomposition point: about 90° C.; $^1$H-NMR (60 MHz, CDCl$_3$, δ): 3.80(3H, s), 6.75(1H, dd, J=3.5 Hz, 7.5 Hz), 6.99(1H, d, J=3.5 Hz), 8.21(1H, d, J=7.5 Hz).

(3) <Production of 2-chloro-6-cyano-4-methoxy pyridine as an intermediate product>

Dimethyl sulfate (8.3 g, 0.070×1 mol) was dropped into 2-chloro-6-cyano-4-methoxy pyridine N-oxide (11.1 g, 0.070 mol). The obtained solution was stirred at room temperature overnight. The solution was washed with diethyl ether by decantation, and then dissolved in 70 ml of water. Sodium cyanide (8.3 g, 0.07 mol×2.4 mol) dissolved in 70 ml of water was dropped into the obtained solution at −10° C. for about one hour in a nitrogen atmosphere. After stirring the reaction solution for 2 hours, the obtained precipitate was filtered out and washed with water. Thus water-washed precipitate was dissolved in ethyl acetate, added with hexane, treated with silica gel and then subjected to distillation to remove the solvent therefrom, thereby obtaining an aimed product.

Yield weight: 6.6 g; yield percentage: 56%; solid; melting point: 94 to 96° C.; $^1$H-NMR (60 MHz, CDCl$_3$, δ): 3.86(3H, s), 6.96(1H, d. J=2 Hz), 7.11(1H, d, J=2 Hz).

(4) <Production of 2-cyano-4-methoxy-6-[3-(trifluoromethyl) phenoxy] pyridine as an intermediate product>

3-(trifluoromethyl) phenol (3.74 g, 0.0178×1.3 mol) was dissolved in about 20 ml of dimethyl formamide. The obtained solution was further mixed with sodium hydride [0.81 g (ca. 60% in mineral oil), 0.0178×1.1 mol) and then with 2-chloro-6-cyano-4-methoxy pyridine (3.0 g, 0.0178 mol). The resultant solution was stirred at about 110° C. for about 5 hours. The obtained reaction solution was distributed in hexane-saturated sodium bicarbonate water and then washed with saturated brine. The organic phase separated from the solution was dried with anhydrous sodium sulfate, concentrated and purified by silica gel column chromatography (eluting solution: ethyl acetate/hexane), thereby obtaining an aimed product.

Yield weight: 3.74 g; yield percentage: 71%; solid; melting point: 88 to 90° C.; $^1$H-NMR (60 MHz, CDCl$_3$, δ): 3.85(3H, s), 6.54(1H, d. J=2 Hz), 6.94(1H, d, J=2 Hz), 6.9–7.6(4H, complex).

(5) <Production of 4-methoxy-6-[3-(trifluoromethyl) phenoxy] picolinic acid (compound No. VI-1) as an intermediate product>

2-cyano-4-methoxy-6-[3-(trifluoromethyl)phenoxy] pyridine (1.0 g, 0.0034 mol) was suspended in about 10 ml of concentrated hydrochloric acid. The obtained suspension was stirred at about 100° C. for about 2 hours. After being allowed to stand for cooling, the obtained reaction solution was mixed with water, and then distributed in ethyl acetate-water. The organic phase separated from the solution was washed with saturated brine, dried with anhydrous sodium sulfate, concentrated and then purified by silica gel column chromatography (eluting solution: ethyl acetate/hexane), thereby obtaining an aimed product.

Yield weight: 0.92 g; yield percentage: 86%.

REFERENCE PRODUCTION EXAMPLE 11

Production of 4-chloro-6-[3-(trifluoromethyl) phenoxy] picolinic acid (compound No. VI-5)

(1) <Production of 4-chloro-6-[3-(trifluoromethyl)phenoxy] picolinic acid methyl ester as an intermediate product>3-(trifluoromethyl) phenol (3.15 g, 0.0019 mol) was dissolved in 50 ml of dried dioxane. Sodium hydride (0.8 g (ca. 60% in mineral oil), 0.0019×1.05 mol) was added to the obtained solution at room temperature. After completion of the foaming, a solution obtained by dissolving 4,6-dichloro picolinic acid methyl ester (4.0 g, 0.0019 mol) in 5 ml of dried dioxane, was dropped into the above solution. Successively, copper iodide (3.7 g, 0.0019×1.0 mol) was added to the obtained solution. The resultant mixture was heated and stirred at a temperature of 120 to 130° C. for 10 hours. Thereafter, the obtained reaction solution was cooled, mixed with 10 ml of water, and then filtered through a glass filter provided with Hyflo Super-Cell. The obtained filtrate was extracted with 100 ml of ethyl acetate two times, thereby separating an organic phase therefrom. The obtained organic phase was dried with sodium anhydride. After the dried organic phase was subjected to distillation to remove the solvent therefrom, the obtained distillation residues were purified by silica gel column chromatography (eluting solution: ethyl acetate/hexane), thereby obtaining an aimed product.

Yield weight: 3.14 g; yield percentage: 49%; solid; melting point: 81 to 82° C.; $^1$H-NMR (60 MHz, CDCl$_3$, δ): 3.83(3H, s), 7.00(1H, d, J=2 Hz), 7.2–7.6(4H, complex), 7.75(1H, d, J=2 Hz).

(2) <Production of 4-chloro-6-[3-(trifluoromethyl)phenoxy] picolinic acid (compound No. VI-5)>

4-chloro-6-[3-(trifluoromethyl)phenoxy] picolinic acid methyl ester (3.1 g, 0.0093 mol) was dissolved in 40 ml of ethanol. 4 ml of an aqueous solution of sodium hydroxide (0.41 g, 0.0093×1.1 mol) was added to the obtained solution. The resultant mixture was heated and stirred at 60° C. for 20 minutes. Thereafter, the obtained reaction solution was cooled and distilled under reduced pressure to remove ethanol therefrom. The obtained residual solution was treated with concentrated hydrochloric acid so as to adjust the pH thereof to 3. The precipitated solids were filtered out from the above residual solution, washed with water and then dried, thereby obtaining an aimed product.

Yield weight: 2.57 g; yield percentage: 87%; solid; melting point: 119 to 120° C.; $^1$H-NMR (60 MHz, DMSO-d$_6$, δ): 4.3–4.9(1H, br), 7.28(1H, d, J=2 Hz), 7.5–7.3(4H, complex), 7.63(1H, d, J=2 Hz).

REFERENCE PRODUCTION EXAMPLE 12

Production of 4-[methyl(phenylmethyl)amino]-6-[3-(trifluoromethyl)phenoxy] picolinic acid (compound No. VI-6)

(1) <Production of 2-bromo-4-[methyl(phenylmethyl)amino]- 6-[3-(trifluoromethyl)phenoxy] pyridine as an intermediate product>

3-(trifluoromethyl) phenol (1.56 g; 0.0080×1.2 mol) was dissolved in dimethyl formamide (about 20 ml). Further, sodium hydride [0.34 g (ca. 60% in mineral oil), 0.0080× 1.06 mol] and then 4-[methyl(phenylmethyl)amino]-2,6-dibromo pyridine (2.85 g, 0.0080 mol) were added to the solution. The obtained solution was refluxed for about 6 hours and, thereafter, allowed so as to stand and cooled to room temperature. The obtained reaction solution was distributed in hexane-saturated sodium bicarbonate water. The organic phase separated from the reaction solution was washed with saturated brine, and dried with anhydrous sodium sulfate. The resultant solution was concentrated and then purified by silica gel column chromatography (eluting solution: ethyl acetate/hexane), and the obtained purified product was subjected to recrystallization using hexane, thereby obtaining an aimed product.

Yield weight: 2.15 g; yield percentage: 61%; solid; melting point: 84 to 87° C.; $^1$H-NMR (60 MHz, CDCl$_3$, δ): 2.92(3H, s), 4.38(3H, s) 5.95(1H, d, J=2 Hz), 6.48(1H, d, J=2 Hz), 6.7–7.6(9H, complex).

(2) <Production of 4-[methyl(phenylmethyl)amino]-6-[3-(trifluoromethyl)phenoxy] picolinic acid (compound No. VI-6)>

2-bromo-4-[methyl(phenylmethyl)amino]-6-[3-(trifluoromethyl)phenoxy] pyridine (6.38 g, 0.0146 mol) was suspended in about 300 ml of diethyl ether. While cooling in a dry ice-acetone bath in an argon atmosphere, the obtained suspension was mixed with n-butyl lithium [10 ml (ca. 1.63M hexane solution), 0.0146×1.1 mol], and the obtained suspension was stirred for about 10 minutes. After replacing an interior of the reactor with a carbon dioxide gas, the solution was removed from the bath and stirred at room temperature for about one hour. The obtained reaction solution was mixed with about 30 ml of a 1N aqueous hydrochloric acid solution, distributed in ethyl acetate-water, and then washed with saturated brine. The organic phase separated from the solution was dried with anhydrous sodium sulfate, concentrated and purified by silica gel column chromatography (eluting solution: ethyl acetate/hexane), thereby obtaining an aimed product.

Yield weight: 3.09 g; yield percentage: 53%; solid; melting point: 80 to 82° C.; $^1$H-NMR (60 MHz, CDCl$_3$, δ): 3.05(3H, s), 4.52(2H, s) 6.18(1H, d, J=2 Hz), 6.7–7.6(10H, complex), 9.83(1H, s).

REFERENCE PRODUCTION EXAMPLE 13

Production of 5-methoxy-6-[3-(trifluoromethyl) phenoxy] picolinic acid (compound No. VI-10)

(1) <Production of 5-methoxy-6-[3-(trifluoromethyl) phenoxy] picolinic acid methyl ester as an intermediate product>

3-(trifluoromethyl) phenol (1.317 g, 0.0081 mol) was dissolved in 10 ml of dried dimethyl acetamide. While cooling the obtained solution with water, sodium hydride (0.39 g (ca. 60% in mineral oil), 0.0081×1.2 mol) was added to the solution. After completion of the foaming, a solution obtained by dissolving 6-bromo-5-methoxy-2-pyridine carboxylic acid methyl ester (2.0 g, 0.0081 mol) in 10 ml of dried dimethyl acetamide, and then copper iodide (1.55 g, 0.081 mol) were successively added to the solution. The obtained mixture was heated and stirred at 120° C. for 10 hours. Thereafter, the obtained reaction solution was cooled, mixed with 50 ml of water and then with 50 ml of ethyl acetate, and filtered through a glass filter provided with Hyflo Super-Cell. The obtained filtrate was extracted with ethyl acetate to obtain an aimed product. An organic phase was separated from the product, washed with water and then dried with anhydrous sodium sulfate. The dried product was concentrated, and the obtained residues were purified by silica gel column chromatography (eluting solution: ethyl acetate/hexane).

Yield weight: 0.68 g; yield percentage: 26%; solid; melting point: 116 to 118° C.; $^1$H-NMR (60 MHz, CDCl$_3$, δ): 3.76(3H, s), 3.86(3H, s), 7.16(1H, d, J=8 Hz), 7.2–7.5(4H, complex), 7.80(1H, d, J=8 Hz).

(2) <Production of 5-methoxy-6-[3-(trifluoromethyl) phenoxy] picolinic acid (compound No. VI-10)>

5-methoxy-6-[3-(trifluoromethyl)phenoxy] picolinic acid picolinic acid methyl ester (0.7 g, 0.0021 mol) was dissolved in 2.8 ml of ethyl alcohol. One milliliter of an aqueous solution of sodium hydroxide (0.102 g, 0.0021×1.2 mol) was added to the obtained solution. The resultant mixture was heated and stirred at 70° C. for 1.5 hours. After cooling, the obtained reaction solution was mixed with 2 ml of concentrated hydrochloric acid, thereby precipitating solids. The precipitated solids were filtered out from the solution, washed with water and then dried.

Yield weight: 0.63 g; yield percentage: 94%; solid; melting point: 145 to 147° C.; $^1$H-NMR (60 MHz, DMSO-d$_6$, δ): 3.80(3H, s), 7.1–7.6(4H, complex), 7.46(1H, d, J=8 Hz), 7.76(1H, d, J=8 Hz), COOH was unclear.

REFERENCE EXAMPLE 14

Production of 6-[3-(trifluoromethyl)phenoxy] picolinic acid (compound No. VI-11)

(1) <Production of 2-cyano-6-[3-(trifluoromethyl)phenoxy] pyridine as an intermediate product>

3-(trifluoromethyl) phenol (4.21 g, 0.0217×1.2 mol) was dissolved in dimethyl formamide (about 30 ml). Further, sodium hydride (0.95 g (ca. 60% in mineral oil), 0.0217×1.1 mol) and then 2-chloro-6-cyano pyridine (3.00 g, 0.0217 mol) were successively added to the obtained solution. The resultant solution was stirred at about 120° C. for about 4 hours, and then allowed to stand for cooling to room temperature. The obtained reaction solution was distributed in hexane-saturated sodium bicarbonate water. The organic phase separated from the solution was washed with saturated brine, dried with anhydrous sodium sulfate. The obtained solution was concentrated and purified by silica gel column chromatography (eluting solution: ethyl acetate/hexane). The purified product was distilled to remove 3-(trifluoromethyl) phenol contained therein, and then subjected recrystallization using hexane, thereby obtaining an aimed product.

Yield weight: 4.34 g; yield percentage: 76%; solid; melting point: 47 to 49° C.; $^1$H-NMR (60 MHz, CDCl$_3$, δ): 7.08(1H, d, J=8 Hz), 6.6–7.7(5H, complex), 8.71(1H, t, J=8 Hz).

(2) <Production of 6-[3-(trifluoromethyl)phenoxy] picolinic acid (compound No. VI-11)>

2-cyano-6-[3-(trifluoromethyl)phenoxy] pyridine (3.00 g, 0.011 mol) was suspended in about 15 ml of concentrated hydrochloric acid. The obtained suspension was stirred at about 100° C. for about 2 hours. After being allowed to stand for cooling, the obtained reaction solution was mixed with water, and then distributed in ethyl acetate-water. The organic phase separated from the solution was washed with saturated brine, dried with anhydrous sodium sulfate, concentrated and then purified by silica gel column chromatography (eluting solution: ethyl acetate/hexane), thereby obtaining an aimed product.

Yield weight: 3.02 g; yield percentage: 94%; solid; melting point: 88 to 90° C.; $^1$H-NMR (60 MHz, CDCl$_3$, δ): 6.8–7.6(5H, complex), 7.6–8.2(2H, complex), 10.17(1H, s).

PRODUCTION EXAMPLE 15

Production of 3-chloro-6-[3-(trifluoromethyl) phenoxy] picolinic acid (compound No. VI-12)

(1) <Production of 2,5-dichloro pyridine N-oxide as an intermediate product>

2,5-dichloro pyridine (20 g, 0.135 mol) was dissolved in 240 ml of acetic acid. The obtained solution was mixed with a 31% aqueous hydrogen peroxide solution (92.5 g, 0.135× 6.24 mol), and then stirred at 65° C. for 18 hours. Thereafter, the obtained reaction solution was poured into ice water, and then sodium carbonate was added thereto to form an alkalescent solution. The alkalescent solution was extracted with 200 ml of chloroform two times. The obtained extract solution was washed with 50 ml of a saturated aqueous sodium sulfite solution and then with saturated brine. The obtained solution was distilled to remove the solvent therefrom, thereby obtaining a white solid.

Yield weight: 11.9 g; yield percentage: 54%; solid; melting point: 77 to 80° C.; $^1$H-NMR (60 MHz, CDCl$_3$, δ): 7.15(1H, dd, J=2 Hz, 8 Hz), 7.4(1H, d, J=8 Hz), 8.3(1H, d, J=2 Hz)

(2) <Production of 3,6-dichloro-2-cyano pyridine as an intermediate product>

2,5-dichloro pyridine N-oxide (11.7 g, 0.071 mol) was gradually added into dimethyl sulfate (9 g, 0.071×1.0 mol). The obtained mixture was stirred overnight. Thereafter, the obtained reaction mixture was mixed with 50 ml of ether, and stirred. Then, the ether was removed from the reaction mixture by decantation, and further the residual ether was distilled off from the reaction mixture under reduced pressure. The distillation residues were dissolved in 50 ml of water (solution A). Separately, sodium cyanide (13.77 g, 0.071 mol×4.0 mol) was dissolved in 67 ml of water, and cooled to a temperature of −7° C. to −15° C. in a nitrogen atmosphere. The above-prepared solution A was dropped into the sodium cyanide solution. The obtained solution was stirred at the above temperature range for 1.5 hours, thereby precipitating crystals. The precipitated crystals was filtered out and washed with water. The obtained solid was further washed with a small amount of acetic acid, thereby obtaining an aimed product.

Yield weight: 6.6 g; yield percentage: 54%; solid; melting point: 90 to 92° C.; $^1$H-NMR (60 MHz, CDCl$_3$, δ): 7.4(1H, d, J=8 Hz), 7.8(1H, d, J=8 Hz).

(3) <Production of 3-chloro-2-cyano-6-[3-(trifluoromethyl) phenoxy] pyridine as an intermediate product>

3-(trifluoromethyl) phenol (3.09 g, 0.0173×1.1 mol) was dissolved in 10 ml of dried dioxane. Sodium hydride (0.728 g (ca. 60% in mineral oil), 0.00173×1.05 mol) was added to the obtained solution. After completion of the foaming, a solution obtained by dissolving 3,6-dichloro-2-cyano pyridine (3 g, 0.0173 mol) in 10 ml of dried dioxane, and copper iodide (0.33 g, 0.0173×0.1 mol) were successively added to the solution, and then the obtained mixture was heated and stirred in an oil bath maintained at 110° C., for 5 hours. Thereafter, the obtained reaction solution was distilled under reduced pressure. The obtained distillation residues were mixed with 30 ml of water, and filtered through a glass filter provided with Hyflo Super-Cell. The obtained filter cake was washed with ethyl acetate, and further a filtrate obtained therefrom was extracted with ethyl acetate. The resultant extract solution was distilled under reduced pressure to remove the solvent therefrom, thereby obtaining a solid product.

Yield weight: 4.26 g; yield percentage: 82%; solid; melting point: 63 to 65° C.; $^1$H-NMR (60 MHz, CDCl$_3$, δ): 7.1(1H, d, J=8 Hz), 7.1–7.6(4H, complex), 7.8(1H, d, J=8 Hz).

(4) <Production of 3-chloro-6-[3-(trifluoromethyl)phenoxy] picolinic acid (compound No. VI-12)>

3-chloro-2-cyano-6-[3-(trifluoromethyl)phenoxy] pyridine (2.58 g, 0.086 mol) was dissolved in 30 ml of 90% sulfuric acid. The obtained solution was heated and stirred at 120° C. for 1.5 hours. Thereafter, the obtained reaction solution was poured into ice water, and then treated with sodium carbonate to form a weakly-acidic solution, thereby precipitating solids. The precipitated solids were filtered out, washed with water and then dried.

Yield weight: 1.68 g; yield percentage: 61%; solid; melting point: 80 to 83° C.; $^1$H-NMR (60 MHz, CDCl$_3$, δ): 7.1(1H, d, J=9 Hz), 7.2–7.5(4H, complex), 7.8(1H, d, J=9 Hz), 9.6(1H, brs).

PRODUCTION EXAMPLE 16

Production of 4-methyl-6-[3-(trifluoromethyl)-phenoxy] picolinic acid (compound No. VI-13)

(1) <Production of 2-chloro-4-methyl pyridine as an intermediate product>

2-hydroxy-4-methyl pyridine (20.3 g, 0.186 mol) was heated and stirred in about 50 ml of phosphorus oxychloride at 100° C. for 4 hours. The obtained reaction solution was poured into ice water, and then sodium carbonate was added thereto to form an alkalescent solution. The obtained alkalescent solution was extracted with 200 ml of chloroform two times. The obtained extract solution was washed with saturated brine, dried with anhydrous sodium sulfate, and then distilled under reduced pressure to remove the solvent therefrom. The distillation residues were purified by silica gel column chromatography (eluting solution: ethyl acetate/hexane), thereby obtaining an aimed product.

Yield weight: 23 g; yield percentage: 97%; oily substance; $^1$H-NMR (60 MHz, CDCl$_3$, δ): 2.26(3H, s), 6.8–7.1(2H, complex), 8.1(1H, d, J=4 Hz).

(2) <Production of 2-chloro-4-methyl pyridine N-oxide as an intermediate product>

2-chloro-4-methyl pyridine (24.0 g, 0.188 mol) was dissolved in 240 ml of acetic acid. The obtained solution was mixed with a 31% aqueous hydrogen peroxide solution (203.9 g, 0.188×9.9 mol), and then stirred at 65° C. for 18 hours. Thereafter, the obtained reaction solution was poured into ice water, and then sodium carbonate was added thereto to form an alkalescent solution. The obtained alkalescent solution was extracted with 300 ml of chloroform two times. The obtained extract solution was washed with 100 ml of a saturated aqueous sodium sulfite solution and further with saturated brine, and then distilled to remove the solvent therefrom, thereby obtaining an aimed product including the raw material.

Rough yield weight: 36 g; rough yield percentage: 96%.

(3) <Production of 6-chloro-2-cyano-4-methyl pyridine as an intermediate product>

2-chloro-4-methyl pyridine N-oxide (12 g, 0.0836 mol) was gradually added into dimethyl sulfate (12.5 g, 0.0836× 1.2 mol). The obtained solution was stirred overnight. Thereafter, the obtained reaction mixture was mixed with 40 ml of ether and then stirred. Successively, the ether was removed from the reaction mixture by decantation, and further the residual ether was distilled off from the reaction mixture under reduced pressure. The distillation residues were dissolved in 40 ml of water (solution A). Separately, sodium cyanide (16 g, 0.0836 mol×3.9 mol) was dissolved in 78 ml of water, and cooled to a temperature of −7° C. to −15° C. in a nitrogen atmosphere. The above-prepared solution A was dropped into the sodium cyanide solution. The obtained solution was stirred at the above temperature range for 1.5 hours, thereby precipitating crystals. The precipitated crystals was filtered out and washed with water. The obtained solid was further washed with a small amount of ethyl acetate, thereby obtaining an aimed product.

Yield weight: 6.88 g; yield percentage: 54%; solid; melting point: 96 to 97° C.; $^1$H-NMR (60 MHz, CDCl$_3$, δ): 2.4(3H, s), 7.3(1H, s), 7.4(1H, s).

(4) <Production of 2-cyano-4-methyl-6-[3-(trifluoromethyl) phenoxy] pyridine as an intermediate product>

3-(trifluoromethyl) phenol (1.75 g, 0.0098×1.1 mol) was dissolved in 5 ml of dried dioxane. Sodium hydride (0.413 g (ca. 60% in mineral oil), 0.0098×1.05 mol) was added to the obtained solution. After completion of the foaming, a solution obtained by dissolving 6-chloro-2-cyano-4-methyl pyridine (1.5 g, 0.0098 mol) in 5 ml of dried dioxane, and copper iodide (0.18 g, 0.0098×0.1 mol) were successively added to the solution, and then the obtained mixture was heated and stirred in an oil bath maintained at 110° C., for 5 hours. Thereafter, the obtained reaction solution was distilled under reduced pressure. The obtained distillation residues were mixed with 15 ml of water, and filtered through a glass filter provided with Hyflo Super-Cell. The obtained filter cake was washed with ethyl acetate, and further a filtrate obtained therefrom was extracted with ethyl acetate. The resultant extract solution was distilled under reduced pressure to remove the solvent therefrom, thereby obtaining an aimed product.

Yield weight: 2.23 g; yield percentage: 82%; oily substance; $^1$H-NMR (60 MHz, CDCl$_3$, δ): 2.4(3H, s), 6.8–7.5 (6H, complex).

(5) <Production of 4-methyl-6-[3-(trifluoromethyl)phenoxy] picolinic acid (compound No. VI-13)>

2-cyano-4-methyl-6-[3-(trifluoromethyl)phenoxy] pyridine (2.055 g, 0.0074 mol) was heated and stirred in 10 ml of concentrated hydrochloric acid and 6 ml of acetic acid at 110° C. for 5 hours. Thereafter, the obtained reaction solution was concentrated under reduced pressure. The obtained residues were mixed with water. The precipitated solids were filtered out, washed with water and then dried, thereby obtaining an aimed product.

Yield weight: 1.49 g; yield percentage: 68%; solid; melting point: 75 to 77° C.; $^1$H-NMR (60 MHz, CDCl$_3$, δ): 2.4(3H, s), 6.8–7.8(6H, complex), 9.6(1H, brs).

The compounds obtained in the above Reference Production Examples 9 to 16 as well as compounds produced according to the methods described therein are shown in Table 24, and the properties and NMR data of these compounds are shown in Tables 25 and 26.

In these Tables, the compounds (VI-5) and (VI-10) were measured by using dimethyl sulfoxide deuteride (DMSO-d$_6$) as a solvent, and the other compounds were measured by using chloroform deuteride (CDCl$_3$) as a solvent.

TABLE 24

| Compound No. | Substituent R$^1$ | Y |
|---|---|---|
| VI-1 | 4-OCH$_3$ | 3-CF$_3$ |
| VI-2 | 4-OCH$_3$ | 3-OCH$_3$ |
| VI-3 | 4-OCH$_3$ | 3-CH$_3$ |
| VI-4 | 4-OCH$_3$ | 3-Cl |
| VI-5 | 4-Cl | 3-CF$_3$ |
| VI-6 | 4-NCH$_3$(CH$_2$Ph) | 3-CF$_3$ |
| VI-7 | 4-NCH$_2$CH$_3$(CH$_2$Ph) | 3-CF$_3$ |
| VI-8 | 4-N(CH$_3$)$_2$ | 3-CF$_3$ |
| VI-9 | 4-SCH$_3$ | 3-CF$_3$ |
| VI-10 | 5-OCH$_3$ | 3-CF$_3$ |
| VI-11 | — | 3-CF$_3$ |
| VI-12 | 3-Cl | 3-CF$_3$ |
| VI-13 | 4-CH$_3$ | 3-CF$_3$ |
| VI-14 | 4-OCH$_3$ | 3-OCF$_3$ |
| VI-15 | 4-OCH$_3$ | 3-SCF$_3$ |

TABLE 25

| Compound No. | Property | NMR 60MHz, δ |
|---|---|---|
| VI-1 | Solid m.p.85–88° C. | 3.84(3H,s),6.55(1H,d, J = 2Hz),7.0–7.6(5H, complex),9.61(1H,s). |
| VI-2 | Solid m.p.80–83° C. | 3.72(3H,s),3.83(3H,s), 6.3–6.9(3H,complex), 6.49(1H,d,J = 2Hz),6.9–7.5 (1H,mult.)7.40(1H,d, J = 2Hz),9.19(1H,s). |
| VI-3 | Solid m.p.93–95° C. | 2.33(3H,s),3.83(3H,s), 6.49(1H,d,J = 2Hz),6.6–7.3 (4H,complex),7.40(1H, d,J = 2Hz),10.02(1H,s). |
| VI-4 | Solid m.p.108–109° C. | 3.83(3H,s),6.51(1H,d, J = 2Hz),6.7–7.4(4H, complex),7.37(1H,d, J = 2Hz),10.07(1H,s). |
| VI-5 | Solid m.p.119–120° C. | 4.38–4.90(1H,br),7.28 (1H,d,J = 2Hz),7.5–7.3 (4H,complex),7.63(1H, d,J = 2Hz). |
| VI-6 | Solid m.p.80–82° C. | 3.05(3H,s),4.52(2H,s), 6.18(1H,d,J = 2Hz),6.7–7.6 (10H,complex),9.83(1H,s). |

TABLE 26

| Compound No. | Property | NMR 60MHz, δ |
|---|---|---|
| VI-7 | Solid m.p.102–104° C. | 1.22(3H,t,J = 7Hz),3.51(2H,q, J =7Hz),4.55(2H,s),6.21(1H,d, J = 2Hz),6.7–7.8(10H,complex), 9.68(1H,s) |
| VI-8 | Solid m.p.141–143° C. | 3.04(6H,s),6.17(1H,d,J = 2Hz), 6.8–7.8(4H,complex),7.21(1H, d,J = 2Hz),10.02(1H,s). |
| VI-9 | Solid m.p.96–99° C. | 2.50(3H,s),6.88(1H,d,J = 2Hz), 7.0–7.7(4H,complex),7.66(1H, d,J = 2Hz),9.40(1H,s). |
| VI-10 | Solid m.p.145–147° C. | 3.80(3H,s),7.1–7.6(4H, complex),7.46(1H,d,J =8Hz), 7.76(1H,d,J = 8Hz),COOH: unclear |
| VI-11 | Solid m.p.88–90° C. | 6.8–7.6(5H,complex),7.6–8.2 (2H,complex),10.17(1H,s). |
| VI-12 | Solid m.p.80–83° C. | 7.1(1H,d,J = 9Hz),7.2–7.5 (4H,complex),7.8(1H,d, J = 9Hz),9.6(1H,brs). |

TABLE 26-continued

| Compound No. | Property | NMR 60MHz, δ |
|---|---|---|
| VI-13 | Solid m.p.75–77° C. | 2.4(3H,s),6.7–7.8(6H, complex),9.6(1H,brs). |
| VI-14 | Solid m.p.103–104° C. | 3.89(3H,s),6.58(1H,d,J = 2Hz), 6.8–7.7(5H,complex), 9.09(1H,s). |

Next, Formulation Examples and Experimental Examples are shown below. However, as apparently understood, carriers (diluents), auxiliaries or adjuvants and mixing ratios therebetween, and effective ingredients of the formulations as shown in these Examples can be varied over a wide range without departing from the scope of the present invention.

"Part" appearing in respective Formulation Examples represents "part by weight".

FORMULATION EXAMPLE 1
(water-disdersible powder)

| Compound No. (I-5) | 50 parts |
|---|---|
| Sodium lignosulfonate | 5 parts |
| Sodium alkylsulfonate | 3 parts |
| Diatomite | 42 parts |

The above components were mixed and pulverized together to prepare a water-dispersible powder. The thus obtained product was used as a water-dispersible powder by diluting with water.

FORMULATION EXAMPLE 2
(emulsion)

| Compound No. (I-6) | 25 parts |
|---|---|
| Xylene | 65 parts |
| Polyoxyethylene alkylaryl ether | 10 parts |

The above components were homogeneously mixed together to prepare an emulsion. The obtained emulsion was used by diluting with water.

FORMULATION EXAMPLE 3
(granules)

| Compound No. (I-39) | 8 parts |
|---|---|
| Bentonite | 40 parts |
| Clay | 45 parts |
| Calcium lignosulfonate | 7 parts |

The above-mentioned components were homogeneously mixed together. The obtained mixture was further kneaded by adding water thereto. The kneaded material was formed into granules by using an ordinary extrusion-type granulator.

EXPERIMENTAL EXAMPLE 1

Experiment for Determination of Herbicidal Effect by Foliage and Soil Treatment (1) <Preparation for Plants to be Tested>

Seeds of redroot pigweed (*Amaranthus retroflexus*), wild mustard (*Sinapis arvensis*), black nightshade (*Solanum nigrum*), cleavers (*Galium aparine*) and ivyleaf speedwell (*Veronica hederaefolia*) were uniformly sowed over a horticultural granular soil (produced by KUREHA CHEMICAL INDUSTRY, CO., LTD.; the same soil was used hereinafter) filled in a planter. The planter was placed in a greenhouse (maintained at a temperature of 19 to 25° C.) to sprout these plants. Two seedlings of each sprouted plant were transplanted to a 10 cm-diameter pot filled with the horticultural granular soil and cultivated in the greenhouse (maintained at a temperature of 19 to 25° C.) until reaching a cotyledonal to bifoliate period suited to the foliage and soil treatment.

(2) <Preparation and Spray of a Test Solution>

Each test compound was dissolved or suspended in acetone. Next, Tween 20 and water were added to the obtained solution or suspension to prepare an aqueous solution as a test solution containing acetone (10% (v/v) and Tween 20 (0.5% (v/v)). Here, the concentration of each test compound in the test solution was adjusted such that the predetermined amount of the test compound was applied to the plants when sprayed at 100 liters/10a. The plants prepared in the above (1) were placed within a frame having a predetermined area, and uniformly sprayed with the test solution using a sprayer such that the amount of each test solution sprayed was 100 liters/10a.

(3) <Evaluation for Herbicidal Effect of Test Compound>

The plants sprayed with the test solution were placed again in the greenhouse (maintained at a temperature of 19 to 25° C.) and cultivated therein. After 14 days, the degree of growth of each plant cultivated in the treated region was compared with that of plant cultivated in non-treated region. The herbicidal activity of each test compound was represented by the rank of the following evaluation criteria:

Rank 1: percentage of weeds killed was less than 20%;

Rank 2: percentage of weeds killed was not less than 20% and less than 50%;

Rank 3: percentage of weeds killed was not less than 50%;

The evaluation results are shown in Table 27.

TABLE 27

| Comp. | | Weed a) | | | | |
|---|---|---|---|---|---|---|
| No. | gal/10a | AR | SA | SN | GA | VH |
| I-5 | 100 | 3 | 3 | 3 | 3 | 3 |
| I-6 | 100 | 3 | 3 | 3 | 3 | 3 |
| I-7 | 100 | 3 | 3 | 3 | 3 | 3 |
| I-14 | 100 | 3 | 3 | 3 | 3 | 3 |
| I-16 | 100 | 3 | 3 | 3 | 3 | 3 |
| I-17 | 100 | 3 | 3 | 3 | 3 | 3 |
| I-18 | 100 | 3 | 3 | 3 | 3 | 3 |
| I-20 | 100 | 3 | 3 | 3 | 3 | 3 |
| I-22 | 100 | 3 | 3 | 3 | 3 | 3 |
| I-30 | 100 | 3 | 3 | 3 | 3 | 3 |
| I-31 | 100 | 3 | 3 | 3 | 3 | 3 |
| I-33 | 100 | 3 | 3 | 3 | 3 | 3 |
| I-35 | 100 | 3 | 3 | 3 | 3 | 3 |
| I-37 | 100 | 3 | 3 | 3 | 3 | 3 |
| I-39 | 100 | 3 | 3 | 3 | 3 | 3 |
| I-40 | 100 | 3 | 3 | 3 | 3 | 3 |
| I-41 | 100 | 3 | 3 | 3 | 3 | 3 |
| I-42 | 100 | 3 | 3 | 3 | 3 | 3 |
| I-48 | 100 | 3 | 3 | 3 | 3 | 3 |
| I-49 | 100 | 3 | 3 | 3 | 3 | 3 |
| I-51 | 100 | 3 | 3 | 3 | 3 | 3 |
| I-54 | 100 | 3 | 3 | 3 | 3 | 3 |
| I-100 | 100 | 3 | 3 | 3 | 3 | 3 |
| I-102 | 100 | 3 | 3 | 3 | 3 | 3 |

AR: redroot pigweed (*Amaranthus retroflexus*);
SA: wild mustard (*Sinapis vensis*);
SN: black nightshade (*Solanum nigrum*);
GA: cleavers (*Galium aparine*): and
VH: ivyleaf speedwell (*Veronica hederaefolia*)

INDUSTRIAL APPLICABILITY

As described above, in accordance with the present invention, there is provided a 6-phenoxy picolinic acid alkylidene hydrazide derivative represented by the general formula (I) which is a novel compound and can be used as an effective ingredient of a herbicide.

What is claimed is:

1. A 6-phenoxy picolinic acid alkylidene hydrazide derivative represented by the general formula (I):

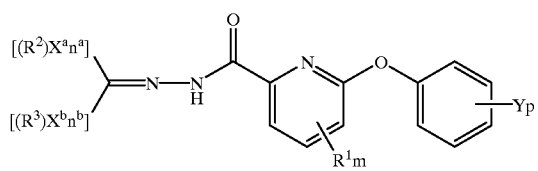

(I)

wherein $R^1$ is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group, a $C_1$ to $C_4$ dialkylamino group or a ($C_1$ to $C_4$ alkyl) ($C_7$ to $C_8$ aralkyl)amino group;

m is an integer of 0 to 3;

$R^2$ and $R^3$ are independently a hydrogen atom or a group which may be substituted with $X^a$ or $X^b$, said group being a $C_1$ to $C_{10}$ alkyl group, a $C_2$ to $C_6$ alkenyl group, a $C_2$ to $C_6$ alkynyl group, a $C_3$ to $C_6$ cycloalkyl group, a phenyl group or an arylalkyl group (whose alkyl moiety has 1 to 3 carbon atoms) [wherein the chain hydrocarbon moiety of each of $R^2$ and $R^3$ is constituted by a longest carbon chain as a main chain, a $C_1$ to $C_4$ alkyl group bonded as a side chain to said main chain is excluded from $R^2$ and $R^3$, and said $C_1$ to $C_4$ alkyl group as a side chain is regarded as substituent of each of $R^2$ and $R^3$];

$X^a$ and $X^b$ are a halogen atom, a $C_1$ to $C_4$ alkoxy group, a $C_1$ to $C_4$ alkylthio group, a $C_1$ to $C_4$ alkyl group (which is not bonded to terminal positions of $R^2$ and $R^3$ when $R^2$ and $R^3$ are a $C_1$ to $C_{10}$ alkyl group), a $C_3$ to $C_6$ cycloalkyl group or a cyano group;

$n^a$ and $n^b$ are 0 or an integer selected from numbers of hydrogen atoms of $R^2$ and $R^3$, respectively, which can be substituted with $X^a$ and $X^b$, respectively;

when both of $R^2$ and $R^3$ are alkyl chains, said $R^2$ and $R^3$ may be directly bonded with each other to form a ring, or said $R^2$ and $R^3$ may be bonded to each other through an oxygen atom, a sulfur atom or a nitrogen atom (the nitrogen atom may be alkylated with a $C_1$ to $C_4$ alkyl group) to form a ring;

Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom; and p is an integer of 0 to 5, and when m, $n^a$, $n^b$ and p are not less than 2, $R^1$s, $X^a$s, $X^b$s and Ys may be the same or different, respectively.

2. A process for producing a 6-phenoxy picolinic acid alkylidene hydrazide derivative represented by the general formula (I), comprising:

subjecting a 6-phenoxy picolinic acid hydrazide derivative represented by the general formula (II) and aldehydes or ketones represented by the general formula (III) to dehydrocondensation

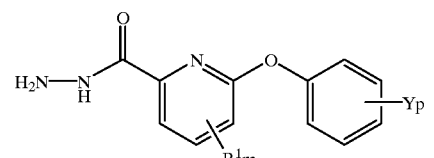

(II)

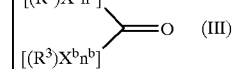

(III)

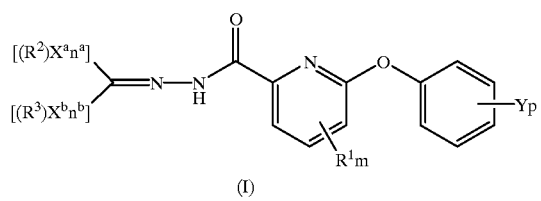

(I)

wherein $R^1$ is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group, a $C_1$ to $C_4$ dialkylamino group or a ($C_1$ to $C_4$ alkyl) ($C_7$ to $C_8$ aralkyl)amino group;

m is an integer of 0 to 3;

$R^2$ and $R^3$ are independently a hydrogen atom or a group which may be substituted with $X^a$ or $X^b$, said group being a $C_1$ to $C_{10}$ alkyl group, a $C_2$ to $C_6$ alkenyl group, a $C_2$ to $C_6$ alkynyl group, a $C_3$ to $C_6$ cycloalkyl group, a phenyl group or an arylalkyl group (whose alkyl moiety has 1 to 3 carbon atoms) [wherein the chain hydrocarbon moiety of each of $R^2$ and $R^3$ is constituted by a longest carbon chain as a main chain, a $C_1$ to $C_4$ alkyl group bonded as a side chain to said main chain is excluded from $R^2$ and $R^3$, and said $C_1$ to $C_4$ alkyl group as a side chain is regarded as substituent of each of $R^2$ and $R^3$];

$X^a$ and $X^b$ are a halogen atom, a $C_1$ to $C_4$ alkoxy group, a $C_1$ to $C_4$ alkylthio group, a $C_1$ to $C_4$ alkyl group (which is not bonded to terminal positions of $R^2$ and $R^3$ when $R^2$ and $R^3$ are a $C_1$ to $C_{10}$ alkyl group), a $C_3$ to $C_6$ cycloalkyl group or a cyano group;

$n^a$ and $n^b$ are 0 or an integer selected from numbers of hydrogen atoms of $R^2$ and $R^3$, respectively, which can be substituted with $X^a$ and $X^b$, respectively;

when both of $R^2$ and $R^3$ are alkyl chains, said $R^2$ and $R^3$ may be directly bonded with each other to form a ring, or said $R^2$ and $R^3$ may be bonded to each other through an oxygen atom, a sulfur atom or a nitrogen atom (the nitrogen atom may be alkylated with a $C_1$ to $C_4$ alkyl group) to form a ring;

Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom; and p is an integer of 0 to 5, and when m, $n^a$, $n^b$ and p are not less than 2, $R^1$s, $X^a$s, $X^b$S and Ys may be the same or different, respectively.

3. A herbicide containing a 6-phenoxy picolinic acid alkylidene hydrazide derivative represented by the general formula (I), as an effective ingredient

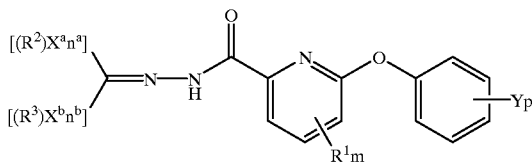

(I)

wherein $R^1$ is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group, a $C_1$ to $C_4$ dialkylamino group or a ($C_1$ to $C_4$ alkyl) ($C_7$ to $C_8$ aralkyl)amino group;

m is an integer of 0 to 3;

$R^2$ and $R^3$ are independently a hydrogen atom or a group which may be substituted with $X^a$ or $X^b$, said group being a $C_1$ to $C_{10}$ alkyl group, a $C_2$ to $C_6$ alkenyl group, a $C_2$ to $C_6$ alkynyl group, a $C_3$ to $C_6$ cycloalkyl group, a phenyl group or an arylalkyl group (whose alkyl moiety has 1 to 3 carbon atoms) [wherein the chain hydrocarbon moiety of each of $R^2$ and $R^3$ is constituted by a longest carbon chain as a main chain, a $C_1$ to $C_4$ alkyl group bonded as a side chain to said main chain is excluded from $R^2$ and $R^3$, and said $C_1$ to $C_4$ alkyl group as a side chain is regarded as substituent of each of $R^2$ and $R^3$];

$X^a$ and $X^b$ are a halogen atom, a $C_1$ to $C_4$ alkoxy group, a $C_1$ to $C_4$ alkylthio group, a $C_1$ to $C_4$ alkyl group (which is not bonded to terminal positions of $R^2$ and $R^3$ when $R^2$ and $R^3$ are a $C_1$ to $C_{10}$ alkyl group), a $C_3$ to $C_6$ cycloalkyl group or a cyano group;

$n^a$ and $n^b$ are 0 or an integer selected from numbers of hydrogen atoms of $R^2$ and $R^3$, respectively, which can be substituted with $X^a$ and $X^b$, respectively;

when both of $R^2$ and $R^3$ are alkyl chains, said $R^2$ and $R^3$ may be directly bonded with each other to form a ring, or said $R^2$ and $R^3$ may be bonded to each other through an oxygen atom, a sulfur atom or a nitrogen atom (the nitrogen atom may be alkylated with a $C_1$ to $C_4$ alkyl group) to form a ring;

Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom; and p is an integer of 0 to 5, and when m, $n^a$, $n^b$ and p are not less than 2, $R^1$s, $X^a$s, $X^b$s and Ys may be the same or different, respectively.

* * * * *